United States Patent
Kiourti et al.

(10) Patent No.: US 11,564,598 B2
(45) Date of Patent: Jan. 31, 2023

(54) SYSTEM AND METHOD FOR MONITORING BODY KINEMATICS

(71) Applicant: Ohio State Innovation Foundation, Columbus, OH (US)

(72) Inventors: Asimina Kiourti, Columbus, OH (US); Vigyanshu Mishra, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 132 days.

(21) Appl. No.: 16/522,594

(22) Filed: Jul. 25, 2019

(65) Prior Publication Data
US 2020/0029863 A1   Jan. 30, 2020

Related U.S. Application Data

(60) Provisional application No. 62/703,021, filed on Jul. 25, 2018.

(51) Int. Cl.
*A61B 5/11* (2006.01)
*A61B 5/00* (2006.01)

(52) U.S. Cl.
CPC .......... *A61B 5/1126* (2013.01); *A61B 5/4528* (2013.01); *A61B 5/6804* (2013.01); *A61B 2503/40* (2013.01); *A61B 2562/0223* (2013.01)

(58) Field of Classification Search
CPC ............... A61B 5/1121; A61B 5/6804; A61B 2562/0223; A61B 5/4585; A61B 5/4528;
(Continued)

(56) References Cited

U.S. PATENT DOCUMENTS

2002/0032386 A1* 3/2002 Sackner ............... A61B 5/0205
600/536
2007/0270722 A1* 11/2007 Loeb .................... A61B 5/1121
600/595
(Continued)

OTHER PUBLICATIONS

Y. Fujita, F. Koshiji and K. Koshiji, "Electromagnetic characteristics of body area network using magnetically-coupled wearable coils worn on bent arm," 2016 International Conference on Electronics Packaging (ICEP), Hokkaido, Japan, 2016, pp. 656-659, doi: 10.1109/ICEP.2016.7486912. (Year: 2016).*
(Continued)

*Primary Examiner* — Sean P Dougherty
*Assistant Examiner* — Jonathan E. Cooper
(74) *Attorney, Agent, or Firm* — Thomas | Horstemeyer, LLP

(57) ABSTRACT

A system and method are provided for monitoring body kinematics. A wearable coil configuration of the system comprises at least first and second electrically-conductive coils adapted to be secured to a subject in a predetermined spatial relationship and orientation relative to one another. The first coil acts as a first transmitter and generates a first magnetic flux when a first electrical current is passed through it. The second coil acts as a receiver. The first magnetic flux induces a first electrical current or voltage in the second coil. A measurement instrument of the system is configured to measure the first electrical current or voltage and to output a first measurement signal. A processor, which may be part of, or external to, the system is configured to execute a motion monitoring algorithm that processes at least the measurement signal to determine at least a first motion made by the subject.

24 Claims, 33 Drawing Sheets

(58) Field of Classification Search
CPC ... A61B 5/459; A61B 2503/40; A61B 5/0022; A61B 5/0024; A61B 5/1114; A61B 2562/0219; A61B 5/11; A61B 5/1116; A61B 5/112; A61B 5/1124
See application file for complete search history.

(56) References Cited

U.S. PATENT DOCUMENTS

| | | | |
|---|---|---|---|
| 2016/0191120 A1* | 6/2016 | Dobyns | H04W 4/80 455/41.1 |
| 2018/0008196 A1* | 1/2018 | Connor | A61B 5/6828 |
| 2019/0101415 A1* | 4/2019 | Sekeljic | A61B 5/6824 |

OTHER PUBLICATIONS

Lee, H. K., Chang, S. I., & Yoon, E. (2009). Dual-mode capacitive proximity sensor for robot application: Implementation of tactile and proximity sensing capability on a single polymer platform using shared electrodes. IEEE sensors journal, 9(12), 1748-1755. (Year: 2009).*

Shinichi Watanabe, Masako Izawa, Akiko Kato, Yan Ropert-Coudert, Yasuhiko Naito. A new technique for monitoring the detailed behaviour of terrestrial animals: A case study with the domestic cat, Applied Animal Behaviour Science, vol. 94, Issues 1-2, (Year: 2005) 2005, pp. 117-131, (Year: 2005).*

Einsmann et al., Modeling a wearable full-body motion capture system, Ninth IEEE International Symposium on Wearable Computers (ISWC'05), 144-151, 2005.

Mukhopadhyay, Wearable Sensors for Human Activity Monitoring: A Review, in IEEE Sensors Journal, vol. 15, No. 3, 1321-1330, 2015.

Shany et al., Sensors-Based Wearable Systems for Monitoring of Human Movement and Falls, in IEEE Sensors Journal, vol. 12, No. 3, 658-670, 2012.

* cited by examiner

SYSTEM AND METHOD FOR MONITORING BODY KINEMATICS

CROSS-REFERENCE TO RELATED APPLICATIONS

This application is a nonprovisional PCT international application that claims priority to, and the benefit of the filing date of, U.S. Provisional Application having Ser. No. 62/703,021, filed on Jul. 25, 2018 and entitled "SYSTEM AND METHOD FOR MONITORING BODY KINEMATICS," which is hereby incorporated by reference herein in its entirety.

GOVERNMENT LICENSE RIGHTS

The invention was made with support of the U.S. Government under Contract/Grant No. 1842531, awarded by the National Science Foundation. The Government has certain rights in this invention.

TECHNICAL FIELD

The present disclosure relates to a wearable system for monitoring body kinematics and associated methods.

BACKGROUND

Joint flexion is an intrinsic part of human motion, with different body parts relying on flexion/extension of different joints (elbow, knee, and so on) to perform activities as diverse as walking, running, climbing, etc. Expectedly, the feasibility of monitoring joint flexion as a function of time opens doors for numerous applications that include, but are not limited to: (a) healthcare (e.g., rehabilitation progress monitoring) (b) sports (e.g., personalized training) (c) gestural recognition (e.g., human-computer interfaces), and consumer electronics (e.g., gaming).

To date, a number of technologies have been reported for monitoring joint flexion. The "gold standard" approach employs camera-based techniques, viz. optical/infrared cameras that track on-body retro-reflective markers, or markerless techniques that use depth-sensitive cameras. These technologies are highly accurate but are restricted to contrived (e.g., lab) environments.

For real-world operation, Inertial Measurement Units (IMUs) have been reported that rely on combinations of accelerometers, gyroscopes and magnetometers. Unfortunately, IMUs suffer from integration drift (error caused by integrating acceleration to derive position) and are obtrusive and not injury-safe (e.g., in case of a fall). Ongoing research on IMUs is geared more toward improving their algorithms rather than the hardware. As an alternative, time-of-flight sensors use body-worn ultrasonic or ultra-wideband transceivers and measure the time taken for transmission as a way to assess distance and, hence, movement. However, they require line-of-sight at all times and are obtrusive.

Finally, bending sensors rely on strain produced upon their constituent material to monitor flexion. This strain can either be converted to equivalent change in resistance, or used on magnetostrictive materials to change permeability and, hence, inductance (Villari effect). They operate in non-contrived settings and do not require line-of-sight. However, they are placed atop the joint thereby restricting natural movement as they bend along with the joint, and raise concerns as to the maximum number of flexes they can withstand.

A need exists for a wearable system for monitoring body kinematics that is: (1) not constrained to the lab environment, (2) capable of working in real time in natural environments, (3) light weight and generally comfortable to the person wearing the system, (4) capable of allowing unrestricted natural movement, (5) safe to the wearer, (6) robust, and (7) capable of precision monitoring.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 18A shows the 3D-printed fixture of FIG. 16A employed in the experimental setup shown in FIG. 18A.

DETAILED DESCRIPTION

Figure 1:
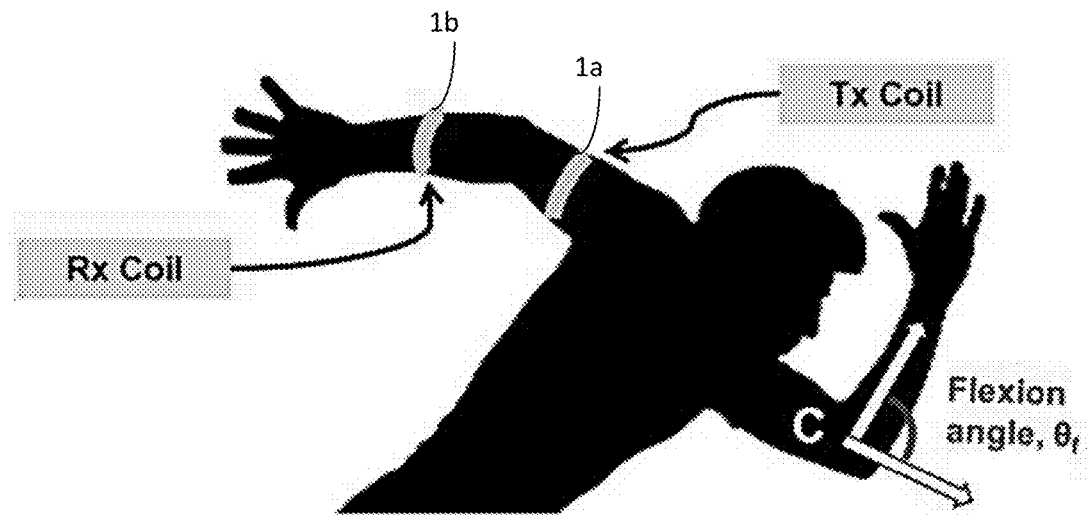
FIG. 1 shows a silhouette of a human being running to whom a transverse coil system configuration, in accordance with a representative embodiment, has been secured to the right arm.

The present disclosure discloses systems and methods for monitoring body kinematics of a body, such as, but not limited to, a body of a human being, for example. A wearable coil configuration of the system comprises at least first and second electrically-conductive coils adapted to be secured to the subject in a predetermined spatial relationship and orientation relative to one another. The first electrically-conductive coil acts as a first transmitter of the system and generates a first magnetic flux when a first electrical current is passed through the first electrically-conductive coil. The second electrically-conductive coil acts as a first receiver of the system. The first magnetic flux induces a first electrical current or voltage in the second electrically-conductive coil.

A measurement instrument of the system is configured to measure the first electrical current or voltage in the second electrically-conductive coil and to output a first measurement signal. A processor that may be part of the system or remote to the system is configured to execute a motion monitoring algorithm that processes at least the first measurement signal to determine at least a first motion made by the subject.

In the following detailed description, for purposes of explanation and not limitation, exemplary, or representative, embodiments disclosing specific details are set forth in order to provide a thorough understanding of the inventive principles and concepts. However, it will be apparent to one of ordinary skill in the art having the benefit of the present disclosure that other embodiments according to the present teachings that are not explicitly described or shown herein are within the scope of the appended claims. Moreover, descriptions of well-known apparatuses and methods may be omitted so as not to obscure the description of the exemplary embodiments. Such methods and apparatuses are clearly within the scope of the present teachings, as will be understood by those of skill in the art. It should also be understood that the word "example," as used herein, is intended to be non-exclusionary and non-limiting in nature.

The terminology used herein is for purposes of describing particular embodiments only, and is not intended to be limiting. The defined terms are in addition to the technical, scientific, or ordinary meanings of the defined terms as commonly understood and accepted in the relevant context.

The terms "a," "an" and "the" include both singular and plural referents, unless the context clearly dictates otherwise. Thus, for example, "a device" includes one device and plural devices. The terms "substantial" or "substantially" mean to within acceptable limits or degrees acceptable to those of skill in the art. For example, the term "substantially parallel to" means that a structure or device may not be made perfectly parallel to some other structure or device due to tolerances or imperfections in the process by which the structures or devices are made. The term "approximately" means to within an acceptable limit or amount to one of ordinary skill in the art. Relative terms, such as "over," "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be below that element.

Relative terms may be used to describe the various elements' relationships to one another, as illustrated in the accompanying drawings. These relative terms are intended to encompass different orientations of the device and/or elements in addition to the orientation depicted in the drawings.

The term "memory" or "memory device", as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor" or "processing device," as those terms are used herein encompass an electronic component that is able to execute a computer program or executable computer instructions. References herein to a system comprising "a processor" or "a processing device" should be interpreted as a system having one or more processors or processing cores. The processor may for instance be a multi-core processor. A processor may also refer to a collection of processors within a single computer system or distributed amongst multiple computer systems. The term "computer," as that term is used herein, should be interpreted as possibly referring to a single computer or computing device or to a collection or network of computers or computing devices, each comprising a processor or processors. Instructions of a computer program can be performed by a single computer or processor or by multiple processors that may be within the same computer or that may be distributed across multiple computers.

To address the aforementioned shortcomings of the state-of-the-art approaches, a new class of coils is disclosed herein that may monitor joint flexion in uncontrived environments while also being seamless, insensitive to line-of-sight, and reliable over time. In accordance with an embodiment, by realizing such coils on e-threads, integration of the coils into daily garments (e.g., shirts, leggings, etc.) is possible to enable monitoring joint flexion on the go.

Most of the human body movements can be broadly categorized into two types of motions: 1) angular change causing change in distance between two body parts (e.g., flexion and extension, abduction and adduction, dorsiflexion and plantarflexion); and 2) rotational motion without change in distance between body parts (e.g., medial and lateral rotation, pronation and supination). If any technology is capable of capturing these two types of motions, i.e., angular and rotational, then it can be designed for monitoring most of the human movements.

With these in mind, the system in accordance with a representative embodiment uses current-carrying coils as transmitter(s) and receiver(s) that are placed upon the human body. The operation is completely wireless and is based on the change of the magnetic flux resulting from change in the coils' relative position as the body moves. In order to demonstrate the inventive principles and concepts, two wearable system configurations are described herein for monitoring human kinematics/motion: a) a transverse coil configuration; and b) a longitudinal coil configuration.

A transverse coil configuration is one that has at least first and second coils that are in planes that are substantially parallel to one another and substantially perpendicular to an axis of the body segment to which the coils are attached when the body segment is in a fully-extended state. For example, the human leg is in the fully-extended state when it is straightened such that the femur and the tibia are nearly aligned along the same axis. In this state, a first coil that is secured around the thigh lies generally in a plane that is substantially parallel to a plane in which a coil secured around the shin generally lies and those planes are substantially perpendicular to an axis along which the femur and tibia generally lie. These coils are "transverse" coils, as that term is used herein.

A longitudinal coil configuration is one that has at least first and second coils that are in planes that are substantially parallel to one another and substantially parallel to an axis of the body segment to which the coils are attached when the body segment is in a fully-extended state. For example, when the human leg is in the fully-extended state, a first coil that is secured to the top of the thigh lies generally in a plane that is substantially parallel to a plane in which a coil secured to the top of the shin generally lies and those planes are substantially parallel to an axis along which the femur and tibia are generally aligned. These coils are "longitudinal" coils, as that term is used herein.

The inventive principles and concepts are hereafter demonstrated within the framework of monitoring the elbow joint kinematics of the right arm, and specifically flexion/extension and pronation/supination rotation of the right arm. The experimental setup involves a cylindrical tissue model 1 representing the upper arm 5 and the forearm 6 joined with a sphere 7 representing elbow. Expectedly, this example is a way of demonstrating the inventive principles and concepts. It should be noted, however, that the inventive principles and concepts are universal and can be applied to any other kind of motion of any body part involving similar or other feasible coil arrangements.

FIG. 1 shows a silhouette of a human being running to whom the transverse coil system configuration, in accordance with a representative embodiment, has been secured to the right arm. In particular, a wrap-around transmission (Tx) coil 1a of the system is attached to the upper arm and a wrap-around receiver (Rx) coil 1b is attached to the forearm. The system and method rely on Faraday's Law of Induction and employ the wrap-around Tx and Rx coils 1a and 1b, respectively, to become angularly misaligned as the joint (i.e., the elbow) flexes.

I. Operating Principle

As shown in FIG. 1, the wrap-around Tx and Rx coils 1a and 1b, respectively, for monitoring joint flexion are wrapped around the limb, positioned right above and below the joint, respectively. The Rx coil 1b receives the signal transmitted by the Tx coil 1a, quantified as the magnitude of the transmission coefficient between the two ($|S_{21}|$). Depending on the frequency of operation, the same two coils 1a and 1b may operate in different modes. That is, the coils 1a and 1b may behave as: (a) antennas (circumference $\lambda$, where $\lambda$ is the operating wavelength), (b) inductive coils (electrically small antennas) (circumference<$0.1\lambda$), or (c) a combination of both ($0.1\lambda$<circumference<$\lambda$). In all cases, $|S_{21}|$ will change as the flexion angle changes. Here, the flexion angle, $\theta_f$ in FIG. 1, is formed between the axes of the upper arm and forearm, meeting at the center of the joint 'C'. Expectedly, the underlying operating principle will change for each mode. As will be discussed next, the inductive mode of operation is identified as optimal for joint flexion monitoring, with the transmission efficiency considerably improving for resonant coils. In this case, if a time-varying current flows through the Tx coil 1a, it will generate a time-varying magnetic flux density passing through the Rx coil 1b. This will induce a voltage on the Rx coil 1b based on Faraday's Law of Induction:

$$V_{Rx} = -\frac{d}{dt}\int\int B_{Tx} \cdot \hat{n}_{Rx} ds \qquad (1)$$

where, $V_{Rx}$ is the voltage induced on the Rx coil 1b, $B_{Tx}$ is the magnetic flux density produced by the Tx coil 1a, and $\hat{n}_{Rx}$ is the normal unit area vector of the Rx coil 1b. As $\theta_f$ changes, $\hat{n}_{Rx}$ changes as well, altering the induced voltage $V_{Rx}$. That is, $V_{Rx}$ changes as a function of $\theta_f$. Equivalently, changes in $V_{Rx}$ can be recorded by a processor (not shown), as discussed below, to monitor $\theta_f$ and, hence, joint flexion. As will be described later, limb rotation can be monitored as well.

II. Simulation and Experimental Setups

A. Simulation Setup

Figures 2A, 2B:
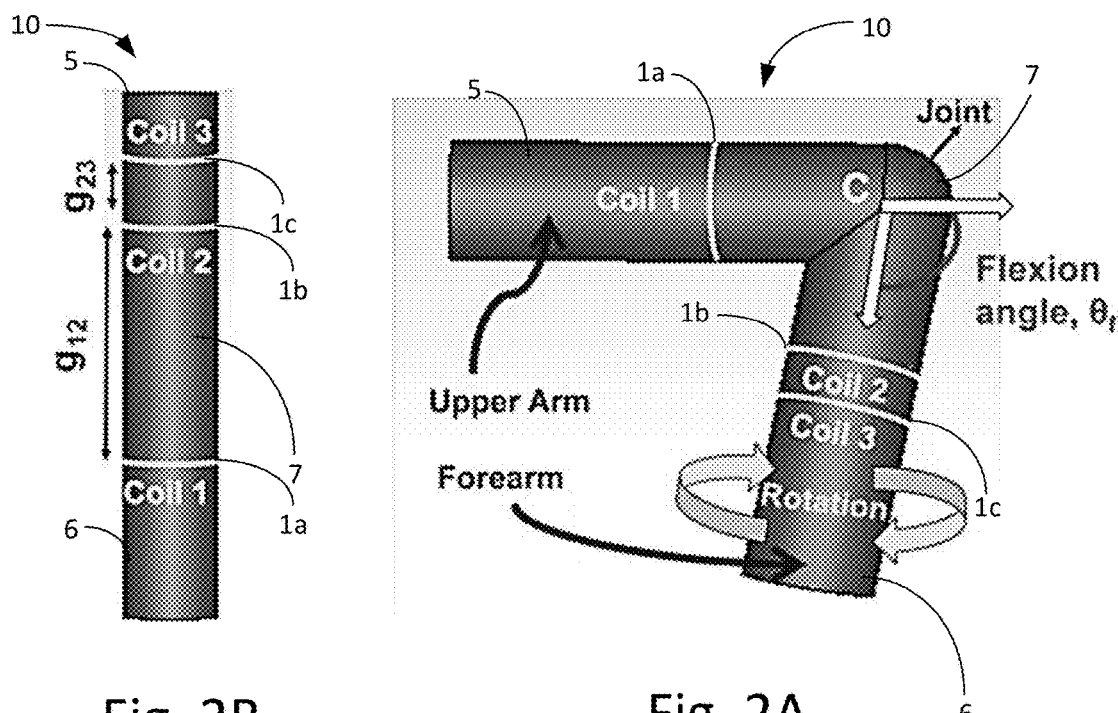
FIGS. 2A and 2B show side and top views, respectively, of a simulation setup for a transverse coil configuration of a wearable system in accordance with a representative embodiment secured to a homogeneous cylindrical model having a portion representing the upper arm of a human and a portion representing the forearm of the human.

FIGS. 2A and 2B show side and top views, respectively, of a simulation setup for a transverse coil configuration of a wearable system in accordance with a representative embodiment secured to a homogeneous cylindrical model 10 having a portion 5 representing the upper arm of a human and a portion 6 representing the forearm of the human. Wrap-around Tx coil 1a acts as a transmitter while wrap-around coils 1b and 1c act as receiver coils. The upper arm 5 and the forearm 6 are modeled as cylinders (3.9 cm in radius, 25 cm in length), while the elbow joint 7 is modeled as a sphere (3.9 cm in radius). The tissue-simulating material is ⅔ muscle, as frequently used in the art to represent the average human body properties.

The wrap-around coils 1a and 1b are single-turn coils placed symmetrically with respect to the joint 7 at a gap, g12, between the two. Both coils 1a and 1b exhibit a radius of 4 cm, are simulated with 30 AWG (0.254 mm-diameter) copper material, and are attached to a lumped capacitor to make them resonant. Optionally, the second Rx coil 1c may be added to improve the system robustness and performance, as will be discussed in detail in Section VI.D. All simulations are carried out using the frequency-domain solver of the CST Microwave Studio® and are based on the Finite Integral Technique. Tetrahedral mesh is used to discretize the computation domain.

B. First Experimental Set-Up

Figure 3A:
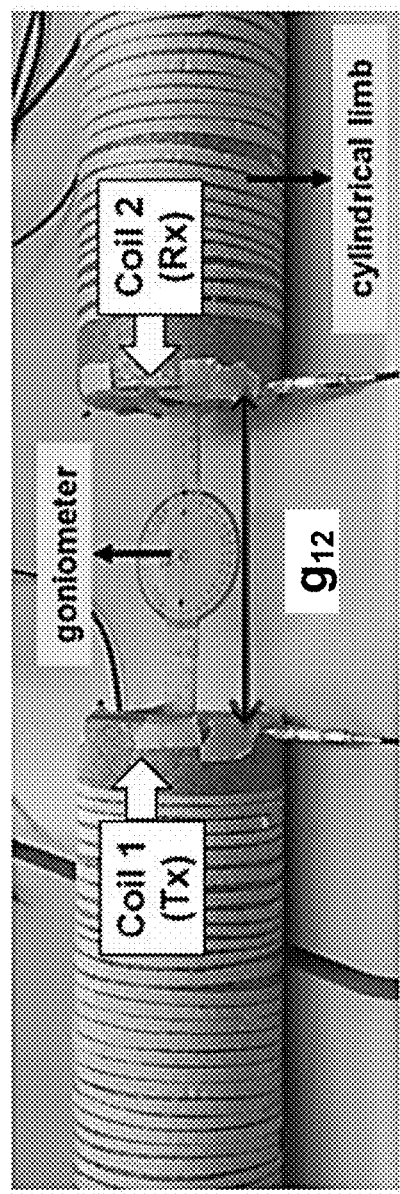
FIGS. 3A-3C are photographs of a first experimental setup model of the transverse coil system configuration
Figure 3B:
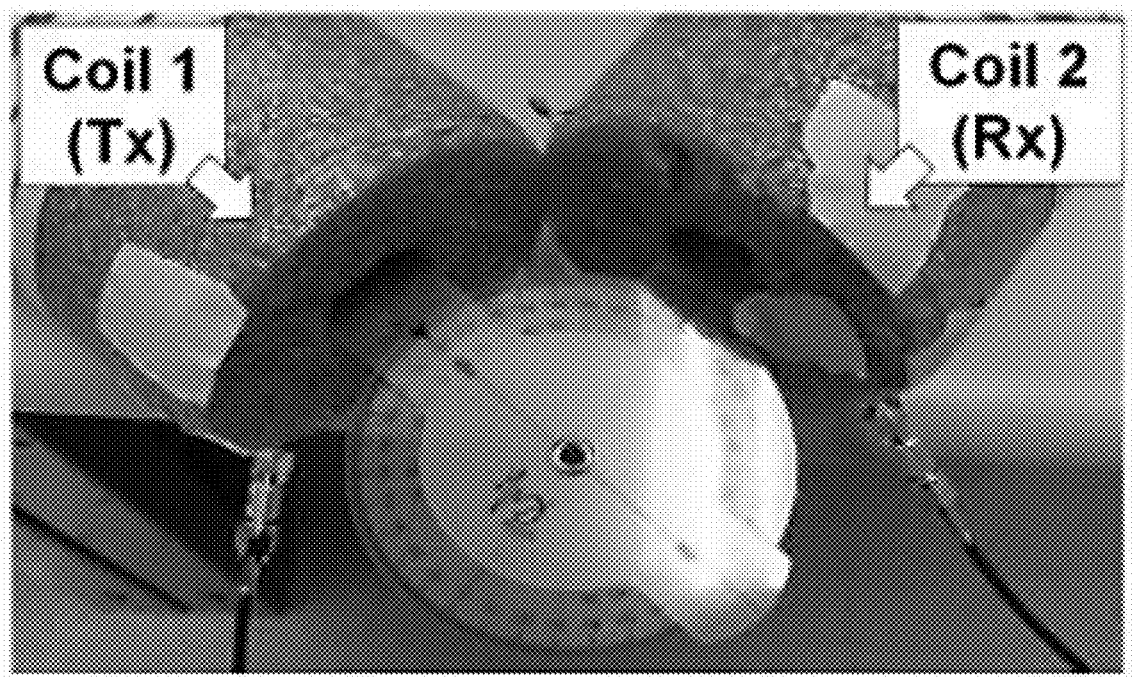
Figure 3C:
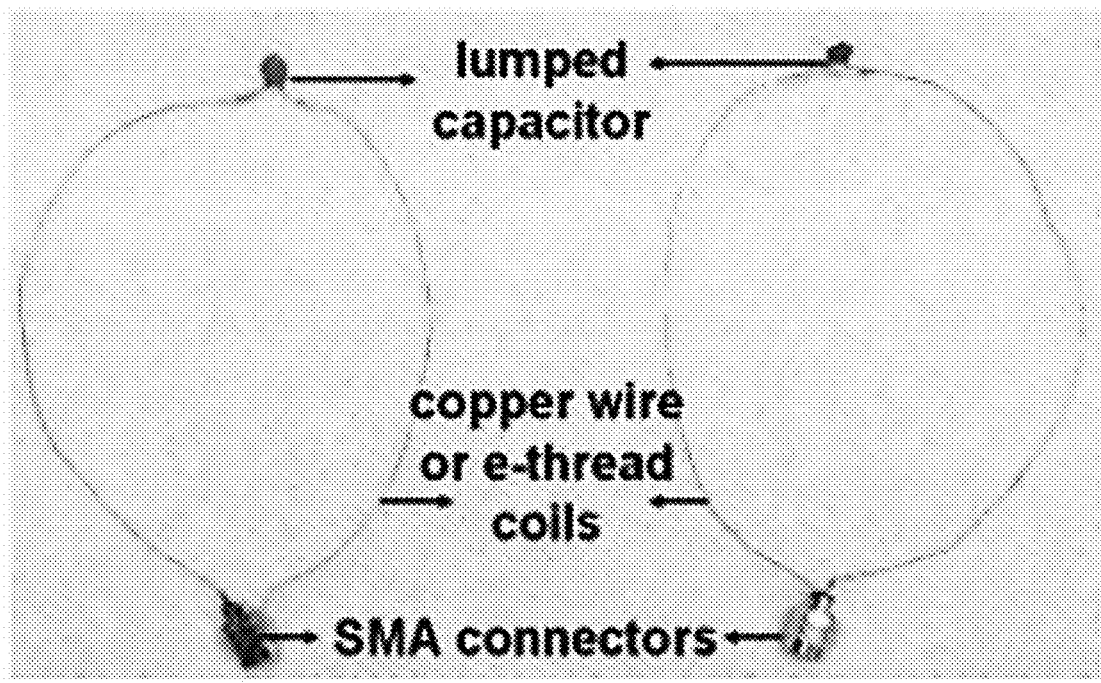

FIGS. 3A-3C are photographs of a first experimental setup model. FIG. 3A shows the fully-extended experimental setup model. FIG. 3B shows the experimental setup model flexed at $\theta_f=100°$. FIG. 3C shows resonant coils of the experimental setup. The upper arm and forearm of the model are realized using cylindrical Styrofoam ($\epsilon r \sim 1$), 4 cm in radius. The choice of material will become clear in Section IV.C. In realizing this phantom, the key challenge lies in implementing a flexion mechanism that accurately emulates the arm's flexion/extension. This is achieved by fixing a goniometer inside of the Styrofoam to emulate the hinge motion. The latter also serves to measure the per case flexion angle (as reference). An example scenario where the joint is flexed by $\theta_f=100°$ is shown in FIG. 3B.

In the experimental setup, the two types of coils (FIG. 3C) are realized, namely, one made of a rigid 30 AWG copper-wire and another made of flexible 40-filament silver-based Liberator e-threads. In both implementations, the wire/e-thread diameter is equal to 0.254 mm, and a lumped capacitor is soldered to make the coils resonant. The Tx (Coil 1) and Rx (Coil 2) are eventually connected to ports 1 and 2 of a PNA-L N5235A network analyzer that records $|S_{21}|$ as a function of flexion angle, $\theta_f$.

III. Proof-Of-Concept Simulation Results

As a proof-of-concept, the simulation setup of FIGS. 2A and 2B is employed (Tx coils 1a and Rx coil 1b only) at an operation frequency of 34 MHz. This frequency falls in the inductive mode of operation, which will be shown in Section IV to be the optimal mode. Lumped capacitors (FIG. 3C) are attached to both coils to make them resonant at the intended frequency. To enable a 0° to 130° flexion range, the coil gap is set to $g_{12}=20$ cm, per FIG. 2B.

Figure 4A:
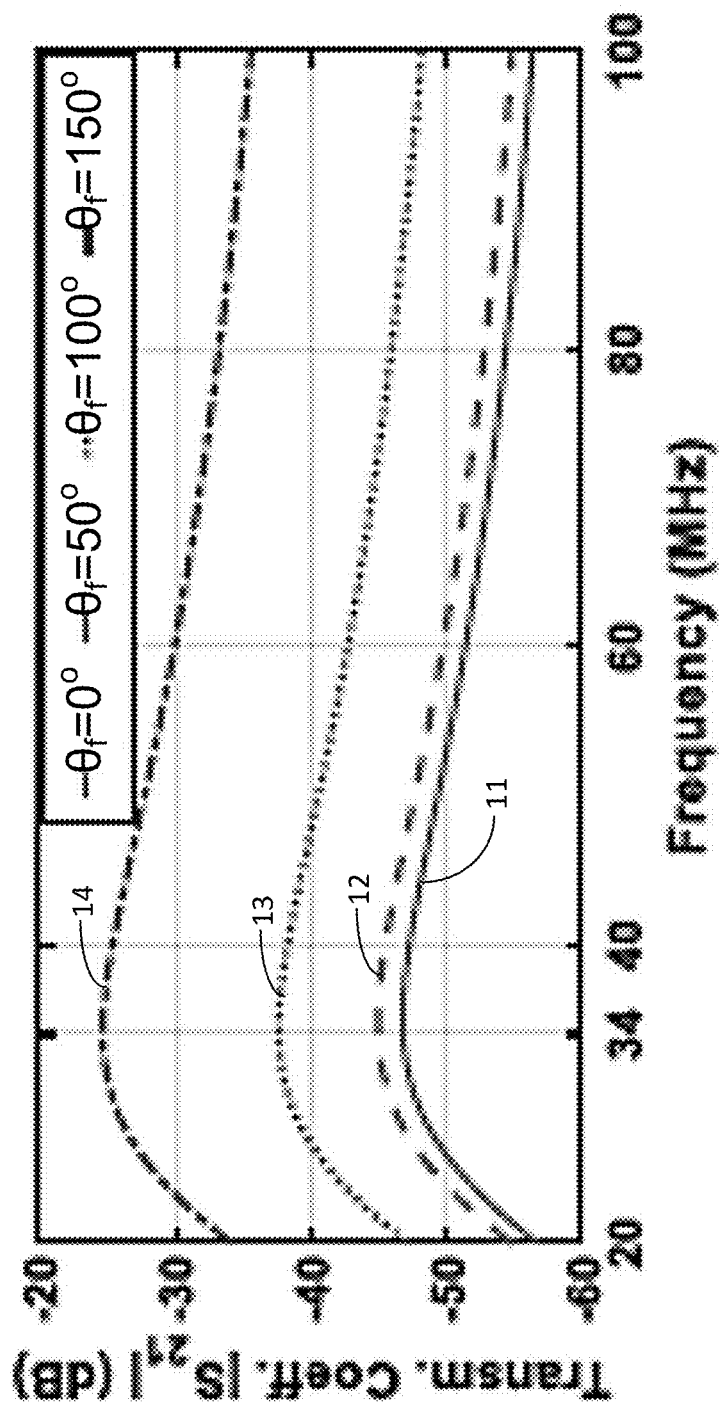
FIGS. 4A and 4B are plots showing proof-of-concept simulation results for 34 MHz resonant transverse coils.
Figure 4B:
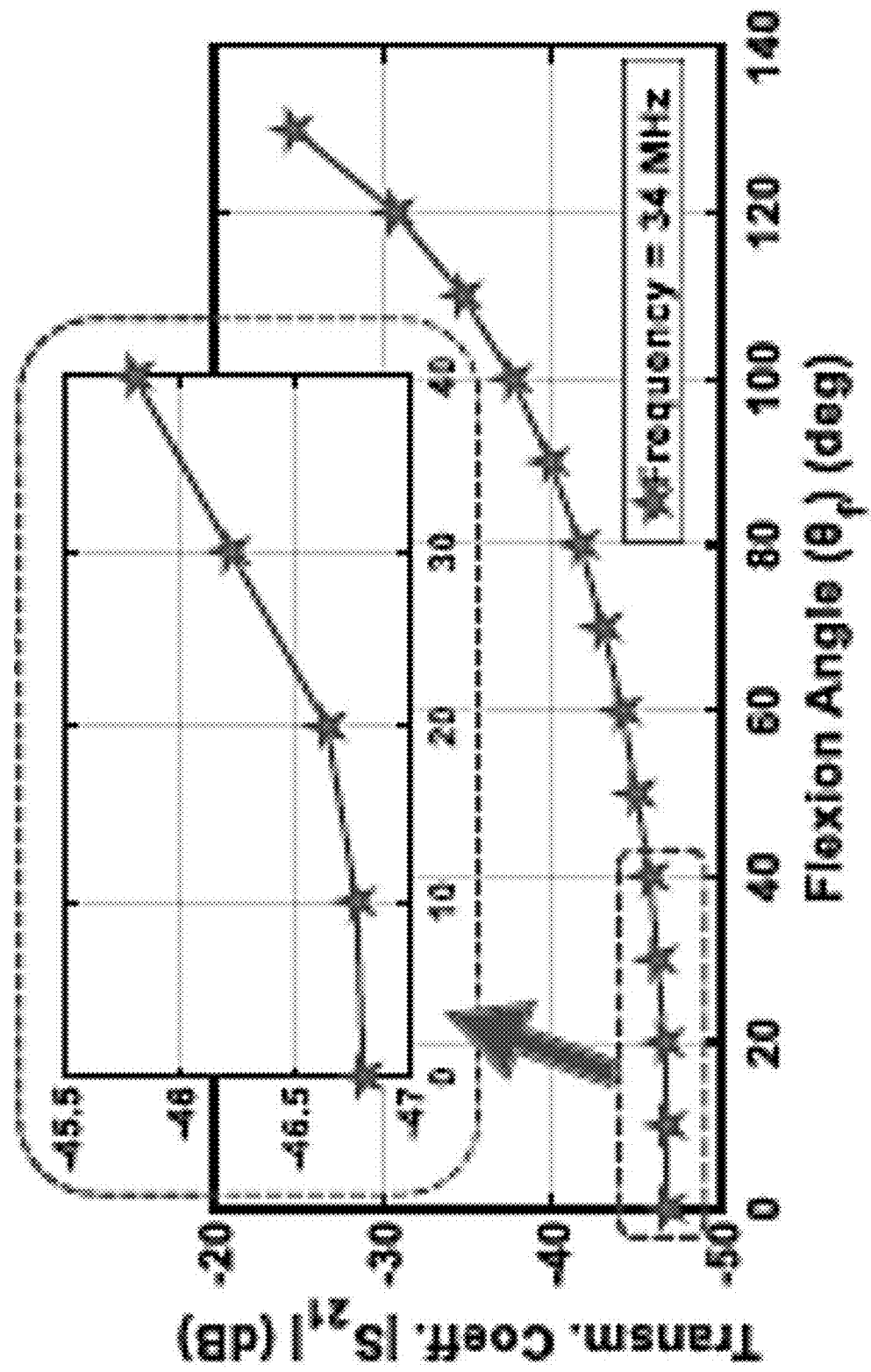

FIGS. 4A and 4B are plots showing proof-of-concept simulation results for 34 MHz resonant transverse coils. FIG. 4A is a plot of transmission coefficient $|S_{21}|$ as a function of frequency at different flexion angles Curves 11, 12, 13 and 14 correspond to $\theta_f=0°$, 50°, 100° and 130°, respectively. FIG. 4B is a plot of transmission coefficient as a function of flexion angle (with zoomed in inset for $\theta_f=0°$ to 40°). Even more importantly, FIG. 4A shows that $|S_{21}|$ at resonance increases with an increase in flexion angle, $\theta_f$. This is more evident in FIG. 4B that plots $|S_{21}|$ as a function of $\theta_f$ at resonance. Notably, there is a one-to-one correlation between $|S_{21}|$ and $\theta_f$, confirming the feasibility of monitoring joint flexion via the present approach.

Simulations for non-resonant coils are also carried out, showing a similar trend to FIG. 4B. Nevertheless, the values of $|S_{21}|$ are significantly lower in this case, e.g., $|S_{21}|$ is degraded by 7 dB at $\theta_f=0°$. That is, non-resonant coils can still be used for flexion monitoring, but the transmit power required to achieve a certain power level on the receive side will be much higher as compared to resonant coils. As such, resonant coils that are inherently capable of optimal power transfer are only considered in this study.

IV. Selection of Optimal Operation Frequency

As mentioned in Section II, the same coils may operate in different modes (antenna, inductive, or combination of the two) depending on the selected operation frequency. Different modes have different advantages and disadvantages for monitoring joint flexion, implying a trade-off for optimal frequency selection. In particular, operating frequency is identified as having significant effect on mainly three parameters, i.e., a) power requirements, b) flexion angle resolution, and c) inter-/intra-subject variability. A thorough study is hereafter presented that explores five representative frequencies (24, 34, 70, 230, and 927 MHz) with respect to the aforementioned parameters. To do so, the simulation setup of FIGS. 2A and 2B is considered (Coils 1a and 1b only). Specifically, at frequencies below 120 MHz, coils of radius 4 cm operate in the inductive mode (circumference<0.1λ). The 927 MHz frequency corresponds to the self-resonance of the coils where they behave as loop antennas, while 230 MHz corresponds to an example frequency in the combined mode of operation.

A. Effect on Power Requirements

Figure 5:
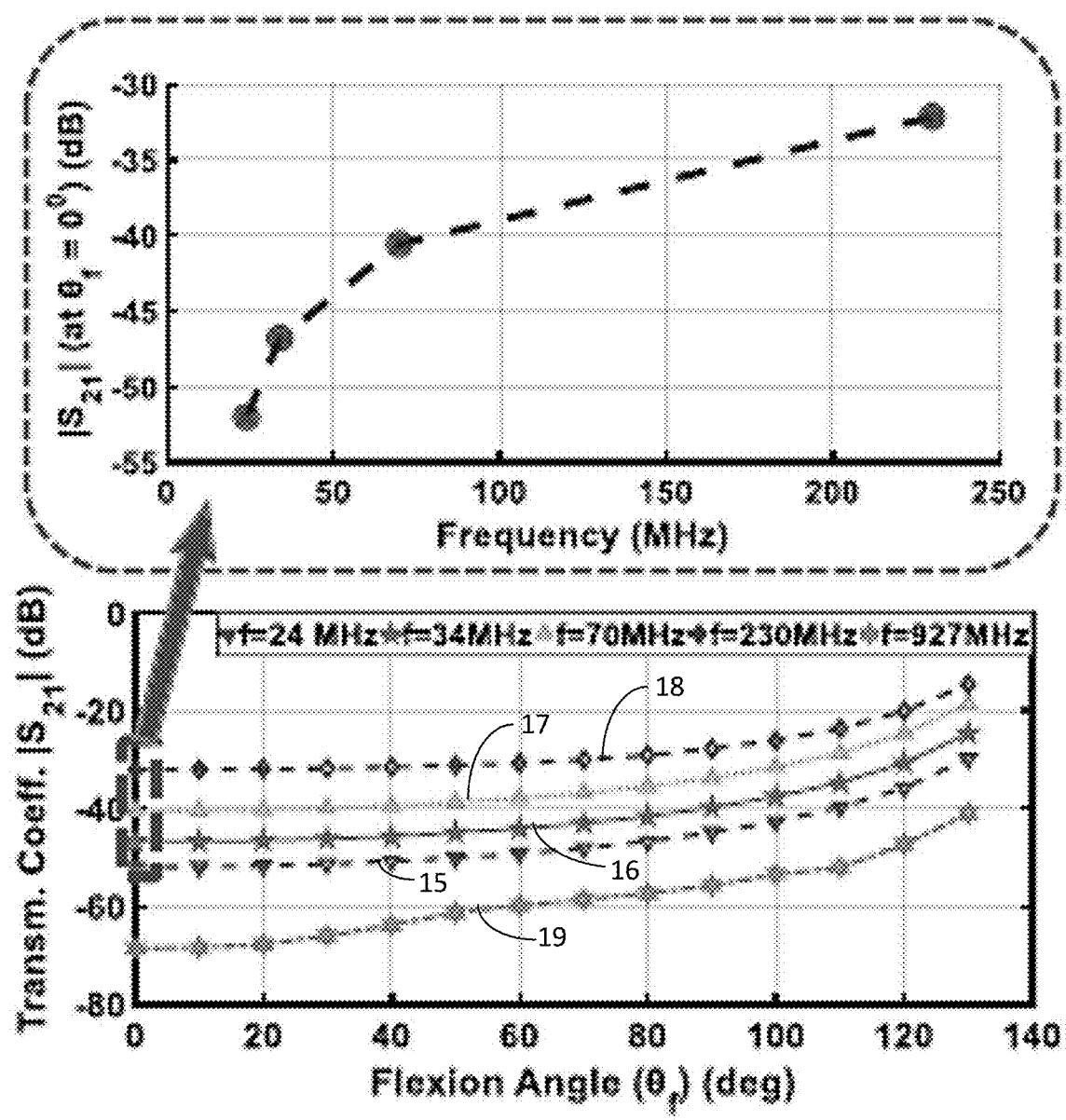
FIG. 5 is a plot of transmission coefficient $|S_{21}|$ as a function of flexion angle $\theta_f$ for various operating frequencies in the inductive, antenna, and combined modes.

FIG. 5 is a plot of transmission coefficient $|S_{21}|$ as a function of flexion angle $\theta_f$ for various operating frequencies in the inductive, antenna, and combined modes. Curves 15, 16, 17, 18 and 19 correspond to operating frequencies 24, 34, 70, 230, and 927 MHz, respectively. Low transmit power is essential for minimizing battery requirements and ensuring conformance to safety standards. Use of resonant coils improves transmission to a great extent (per Section III), while optimal frequency selection may further boost transmission efficiency. FIG. 5 demonstrates the latter. As seen, the antenna mode (927 MHz) does not show a one-to-one correlation between $|S_{21}|$ and $\theta_f$, unlike the inductive and combined modes. Besides, the transmission coefficient, $|S_{21}|$, exhibits the lowest values for this mode making it the least efficient in terms of transmit power. With the above in mind, the antenna mode is considered unsuitable for the intended application. While in the inductive and combined modes, $|S_{21}|$ decreases as the operating frequency is reduced. This can be attributed to changes in impedance matching at different frequencies. Notably, this trend is not linear on the dB scale (see inset of FIG. 5), implying that transmission efficiency significantly drops as frequency decreases. That is, higher frequencies (in the inductive or combined mode) are preferred so as to enable higher received power levels or, equivalently, lower power requirements on the transmitter end.

B. Effect on Flexion Angle

Figure 6:
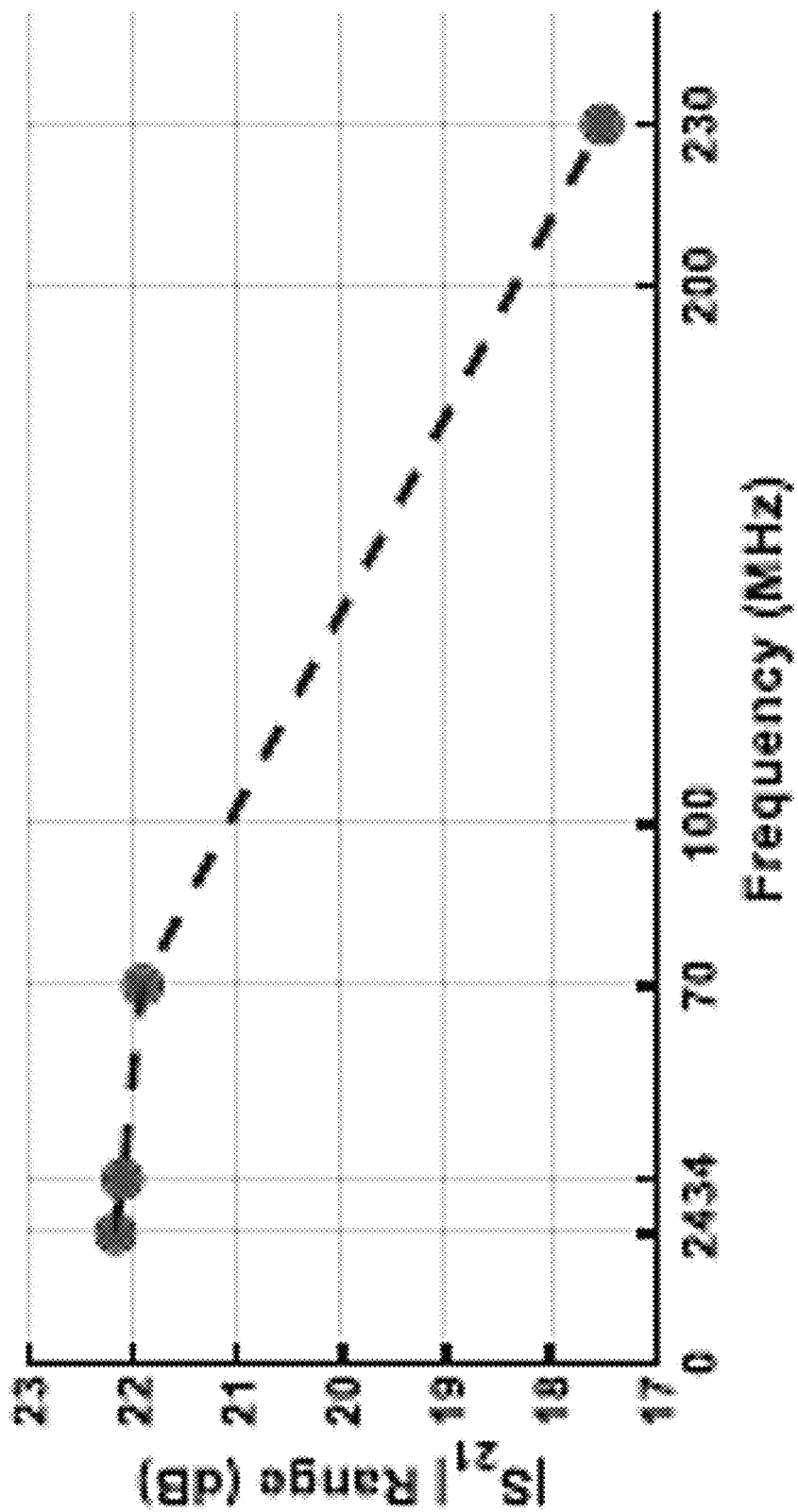
FIG. 6 is a plot of range of transmission coefficient values $|S_{21}|$ calculated by subtracting $|S_{21}|$ at $\theta_f=0°$ from $|S_{21}|$ at $\theta_f=130°$, signifying the system resolution at different frequencies.

FIG. 6 is a plot of range of transmission coefficient values $|S_{21}|$ calculated by subtracting $|S_{21}|$ at $\theta_f=0°$ from $|S_{21}|$ at $\theta_f=130°$, signifying the system resolution at different frequencies. As would be expected, high angular resolution is desired for the designed system, implying that the range of $|S_{21}|$ values corresponding to the extreme 0° and 130° flexion angles should be as large as possible. To better understand how this parameter is affected by the operating frequency, FIG. 6 plots the aforementioned $|S_{21}|$ range (i.e., $|S_{21}|$ at $\theta_f=0°$ subtracted from $|S_{21}|$ at $\theta_f=130°$) for operating frequencies in the inductive and combined mode. As seen, lower frequencies (in the inductive or combined mode) are preferred so as to enable higher angular resolution.

C. Inter-/Intra-Subject Variability

Figure 7A:
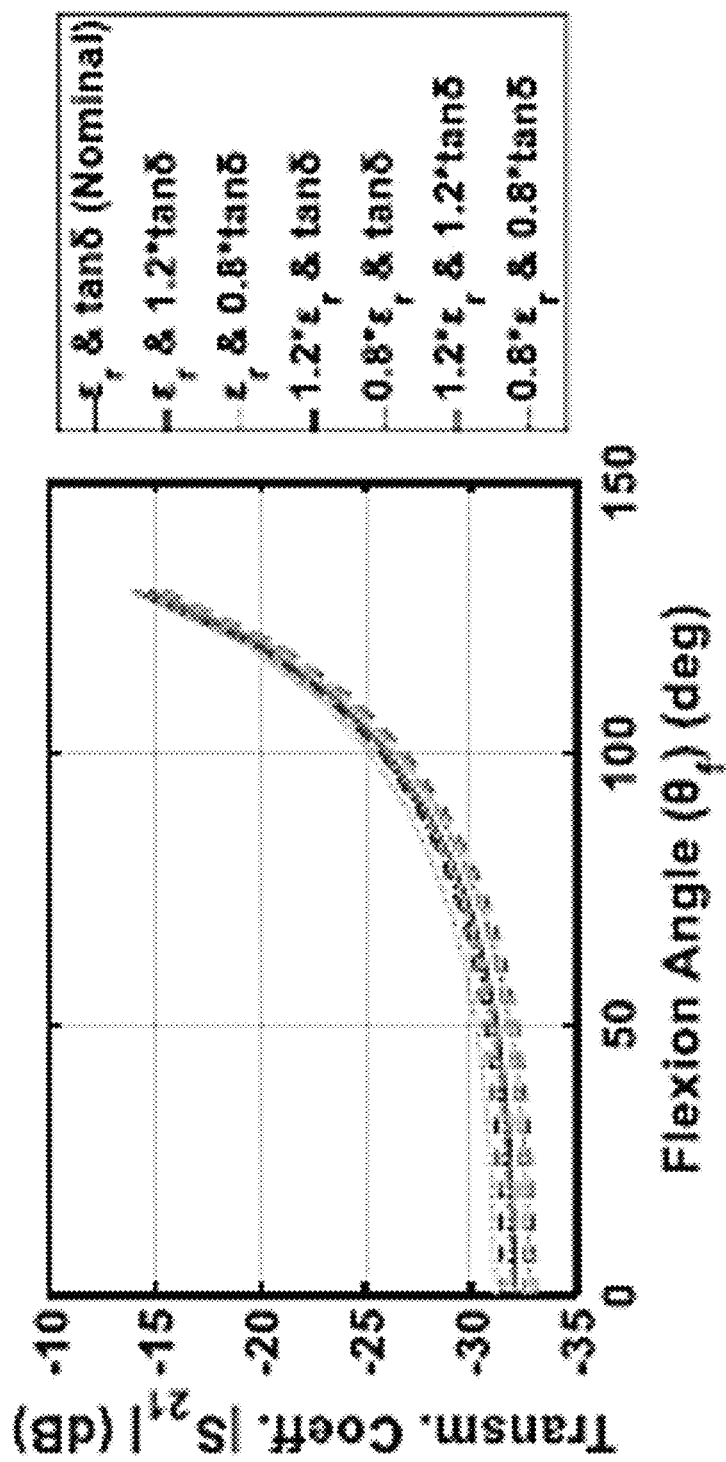
FIGS. 7A and 7B are plots of simulation results for characteristic frequencies in the combined (230 MHz) and inductive (34 MHz) modes, respectively.
Figure 7B:
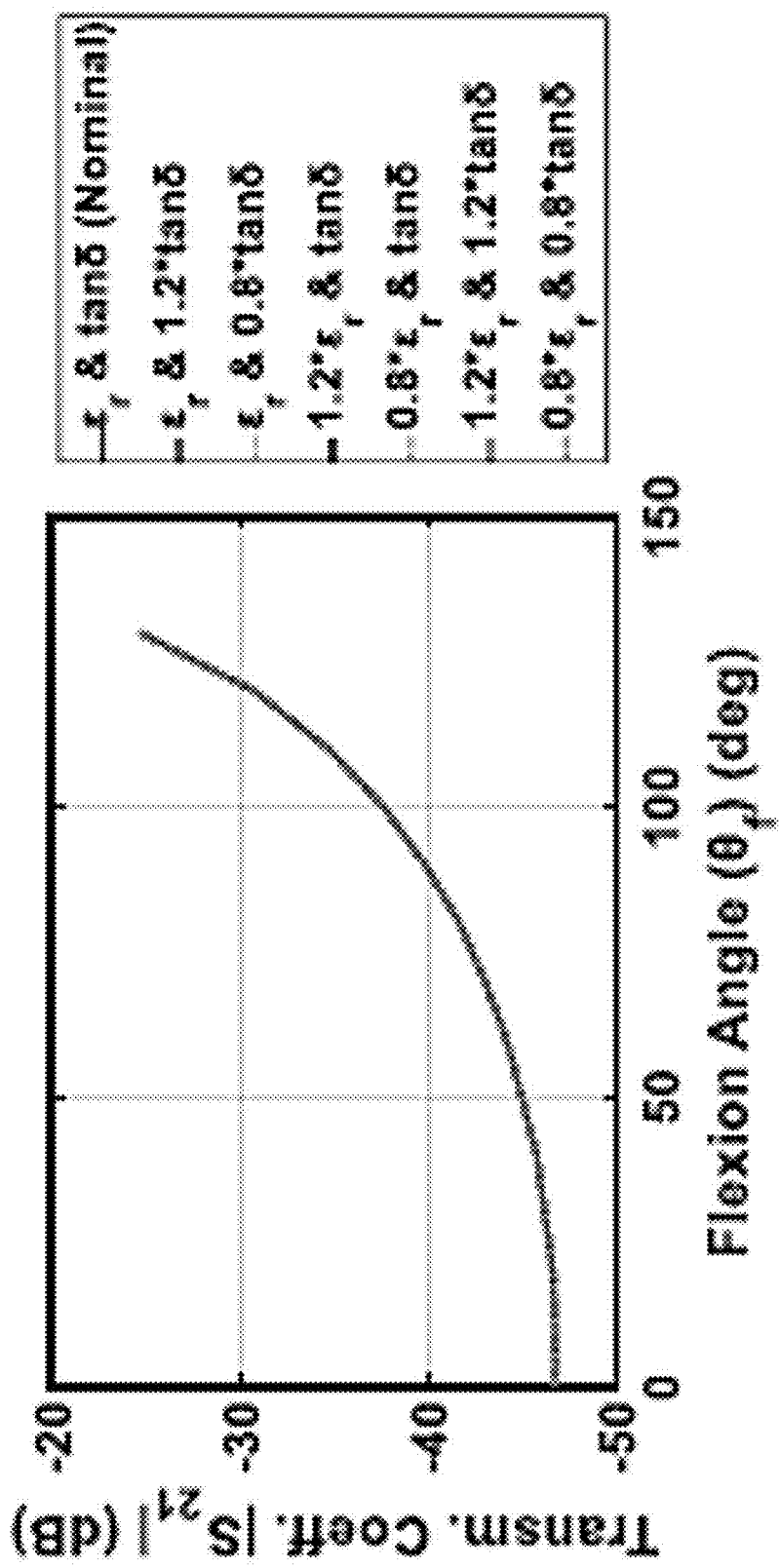

Human tissue properties (permittivity, $\varepsilon_r$, and loss tangent, tan $\delta$) vary from person to person and even from time to time for the same individual. The system ideally should be insensitive to such changes in the underlying tissues. To explore the latter, tissue properties are varied by ±20% from their nominal values (⅔ muscle in FIGS. 2A and 2B). FIGS. 7A and 7B are plots of the change in transmission coefficient values $|S_{21}|$ with ±20% variation in tissue permittivity ($\varepsilon_r$) and loss tangent (tan $\delta$) at 230 MHz and 34 MHz, respectively. Nominal values ($\varepsilon_r$ & tan $\delta$) correspond to ⅔ muscle tissue properties. Simulation results for characteristic frequencies in the combined (230 MHz) and inductive (34 MHz) modes are shown in FIGS. 7A and 7B, respectively. At 230 MHz, $|S_{21}|$ gets considerably impacted by changes in the underlying tissue properties. By contrast, at 34 MHz, $|S_{21}|$ is shown to be extremely robust to changes in the underlying tissues. That is, the results highlight remarkable advantages for the inductive mode. Notably, simulations for air medium used to replace the ⅔ muscle at 34 MHz also indicate an identical pattern to that of FIG. 7B. This is a unique advantage for experimental testing purposes, implying that Styrofoam phantoms (e.g., FIGS. 3A and 3B), rather than tissue-emulating materials, can be employed to validate the sensor. The reason is that coils are inductively coupled via magnetic fields and are not radiating. Since human tissue has a relative permeability of $\mu_r\sim1$, magnetic coupling is not affected by the presence or absence of tissue.

D. Combined Effect and Optimal Frequency Selection

For optimal frequency selection, the effect of all three aforementioned parameters needs to be taken into account. To ensure tolerance to inter-/intra-subject variability and high angular resolution, operation deep in the inductive mode is preferred. On the other hand, for reduced power requirements on the transmit side, higher frequencies in the inductive mode or even the combined mode are preferred. With this trade-off in mind, we herewith select the 34 MHz operating frequency.

V. Experimental Validation

Figure 8:
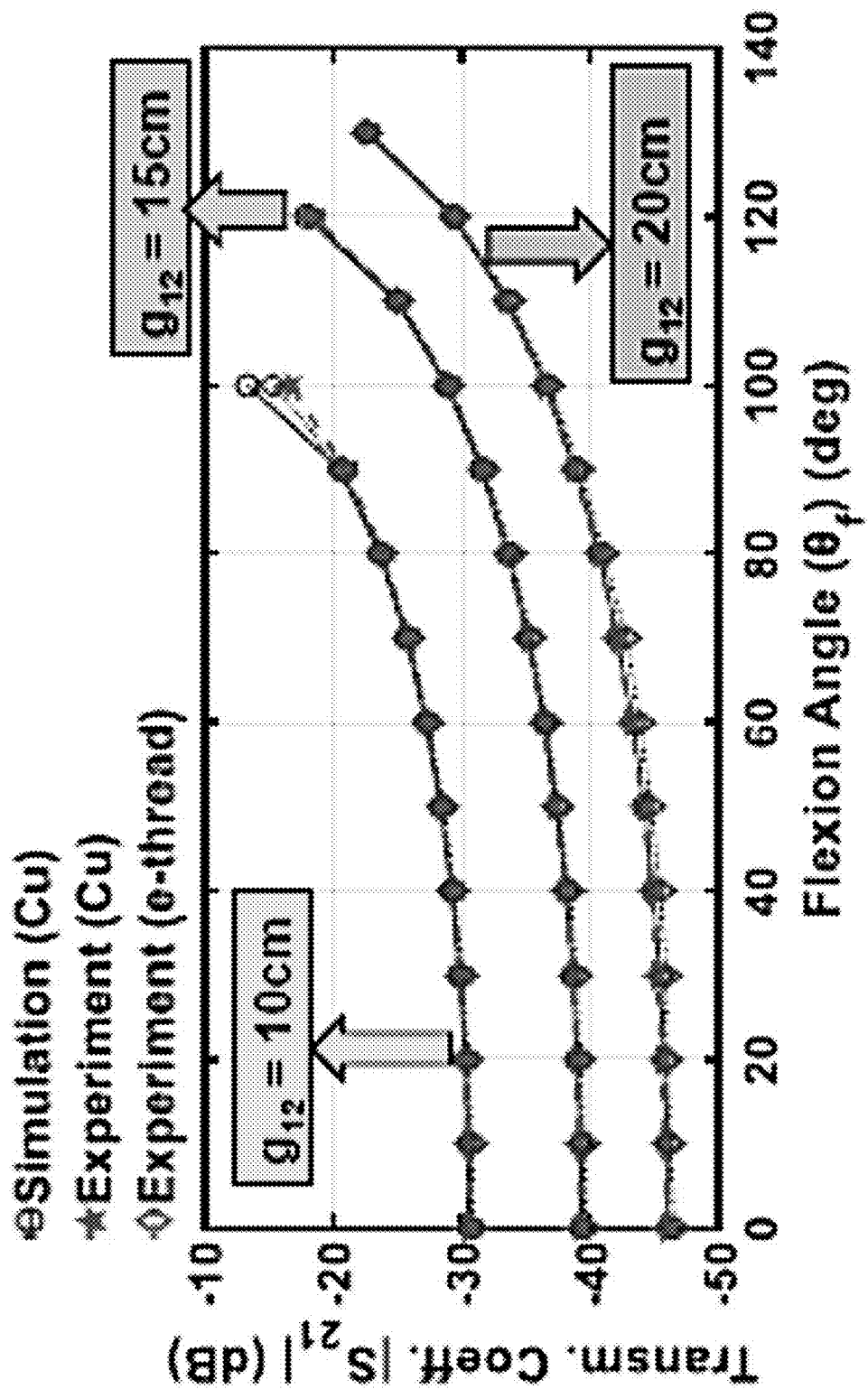
FIG. 8 is a plot summarizing experimental vs. simulation results for copper and experimental results for e-thread coils at 34 MHz at various coil gaps (g12=10, 15, 20 cm).

To validate the simulations, experiments are carried out using the setup shown in FIGS. 3A-3C. The optimal operation frequency of 34 MHz is selected, and coils are made resonant via a lumped capacitor per previous discussions. FIG. 8 is a plot summarizing experimental vs. simulation results for copper and experimental results for e-thread coils at 34 MHz at various coil gaps ($g_{12}$=10, 15, 20 cm). As seen in FIG. 8, excellent agreement is achieved between the simulation and experimental results. Even more importantly, e-thread coils perform identical to their copper counterparts while also being flexible and extremely robust to high/low temperatures, washing/drying, and mechanical duress.

To confirm the validity of the Styrofoam fixture shown in FIGS. 3A and 3B, experiments with a ground beef phantom are also performed at $g_{12}$=15 cm. The ground beef phantom has often been used in the art to accurately emulate the average and frequency-dependent properties of the human body. In this case, average discrepancies vs. simulations for all flexion angles are smaller than 0.07 dB. That is, Styrofoam can indeed by employed as an alternative to tissue-emulating materials.

VI. Additional Considerations

A number of additional factors are explored below, identified as crucial in designing, customizing, increasing the robustness, improving the performance, and ensuring the safety of the proposed system for joint flexion monitoring. The simulation setup of FIGS. 2A and 2B is considered along with resonant coils at 34 MHz.

A. Selection of Coil Gap (g12)

Figure 9:
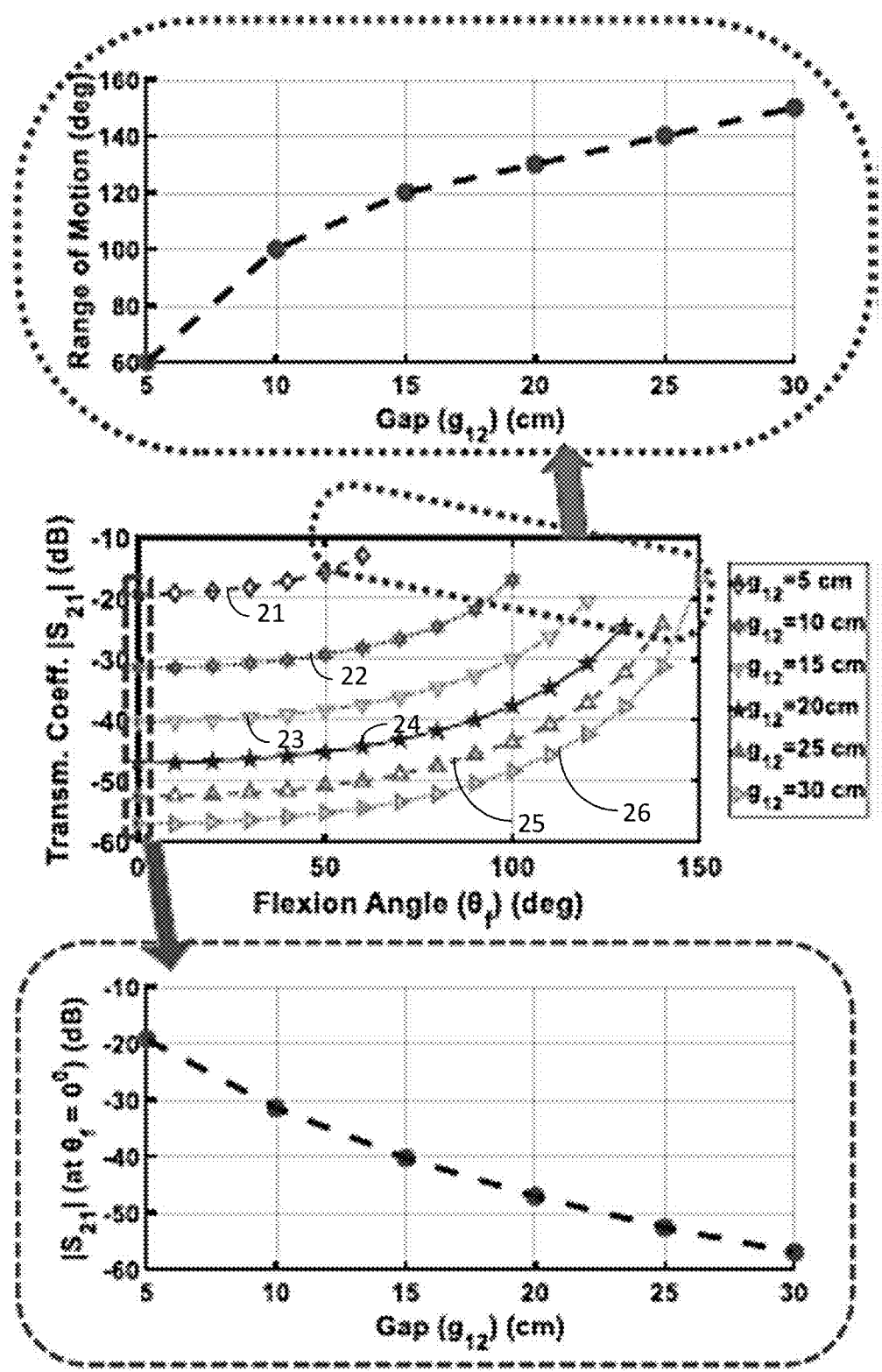
FIG. 9 is a plot of transmission coefficient $|S_{21}|$ as a function of flexion angle for various distances between the coils ($g_{12}$); the top inset of FIG. 9 depicts the trend of increase in range of motion with increasing $g_{12}$; the bottom inset depicts the trend of degradation in $|S_{21}|$ with increasing $g_{12}$.

Selection of coil gap ($g_{12}$ per FIGS. 2A and 2B and FIG. 3A) is a variable design parameter that may be readily optimized per case. The effect of $g_{12}$ on system performance is hereafter discussed with reference to FIG. 9. FIG. 9 is a plot of transmission coefficient $|S_{21}|$ as a function of flexion angle for various distances between the coils ($g_{12}$). The top inset in FIG. 9 depicts the trend of increase in range of motion with increasing $g_{12}$. The bottom inset depicts the trend of degradation in $|S_{21}|$ with increasing $g_{12}$. Curves 21, 22, 23, 24, 25 and 26 in FIG. 9 correspond to g12=5, 10, 15, 20, 25 and 30 cm, respectively. As seen in FIG. 9, a similar one-to-one correlation is observed between $|S_{21}|$ and $\theta_f$ in all cases. That is, either configuration can be employed to monitor joint flexion. Nevertheless, a trade-off comes into play. Referring to the bottom inset of FIG. 9, a decrease in $g_{12}$ leads to a non-linear increase of $|S_{21}|$, and hence lower power requirements. This is expected given the inverse relationship between magnetic field and gap between the coils. However, decrease in $g_{12}$ concurrently reduces the range of motion that can be captured by the coils; as $g_{12}$ gets smaller, coils physically touch each other at smaller flexion angles. The trend is again non-linear and is better illustrated in the top inset of FIG. 9. As an example, for $g_{12}$=5 cm, only angles in the 0° to 60° range can be captured. For $g_{12}$=30 cm, the range expands all the way to 150°, yet with a degradation in $|S_{21}|$ by as high as 38.8 dB, on average. That is, FIG. 9 provides design guidelines for optimal selection of g12 based on the application that the designer may have in hand (e.g., age of the individual, type of joint, power availability, receiver sensitivity, and so on).

B. Effect of Limb Size

Figure 10:
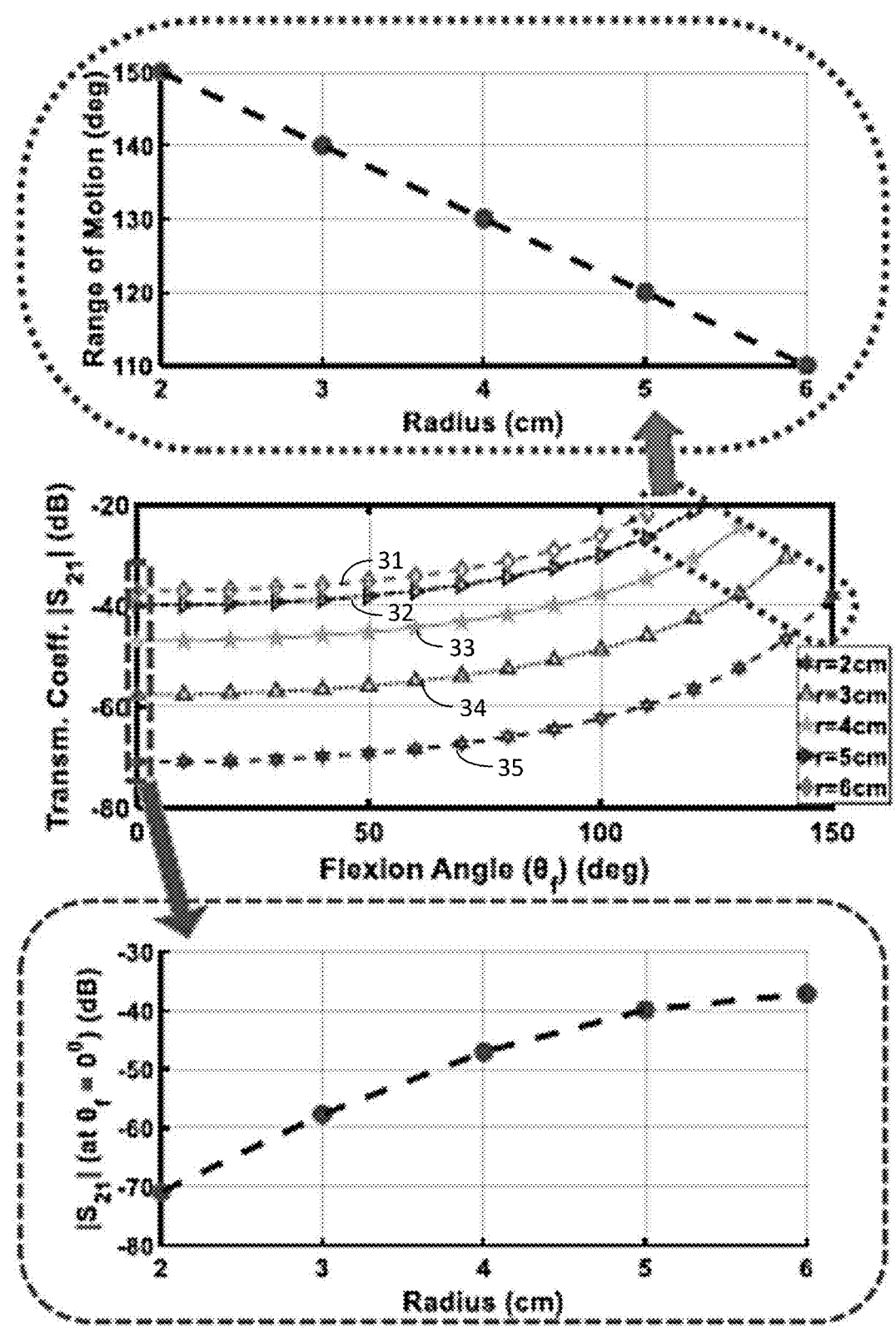
FIG. 10 is a plot of transmission coefficient $|S_{21}|$ as a function of flexion angle for various coil radii; the top inset in FIG. 10 depicts the trend of decrease in range of motion as radius increases; the bottom inset depicts the trend of improvement in $|S_{21}|$ with increasing radius.

Coil radius is directly determined by the underlying limb radius. It is, thus, expected that different coil radii will be employed for different individuals and/or different joints of the same individual. FIG. 10 is a plot of transmission coefficient $|S_{21}|$ as a function of flexion angle for various coil radii. The top inset in FIG. 10 depicts the trend of decrease in range of motion as radius increases. The bottom inset depicts the trend of improvement in $|S_{21}|$ with increasing radius. Curves 31, 32, 33, 34 and 35 correspond to radius, r, equal to 6, 5, 4, 3 and 2 cm, respectively. Along these lines, FIG. 10 demonstrates the effect of varying limb/coil radius (2 to 6 cm) upon the system performance. As expected, a similar one-to-one correlation is observed between $|S_{21}|$ and $\theta_f$ in all cases. That is, the proposed sensor is readily customizable. Nevertheless, system performance will be altered accordingly. Referring to the bottom inset of FIG. 10, an increase in coil radius (viz. thicker limb) leads to a non-linear increase of $|S_{21}|$, and hence lower power requirements. This is expected given the increase in flux linkage associated with increase coil radius. However, increase in coil radius concurrently reduces the range of motion that can be captured by the coils; as radius increases, coils physically touch each other at smaller flexion angles. The trend is illustrated in the top inset of FIG. 10. To sum up, the approach disclosed herein is applicable to any limb size, with limb size impacting the system power requirements and range of motion, per FIG. 10. Of course, system design may be readily fine-tuned per application requirements by tweaking variable parameters, such as the coil gap depicted in FIG. 9.

C. Robustness to Limb Rotation

Figure 11:
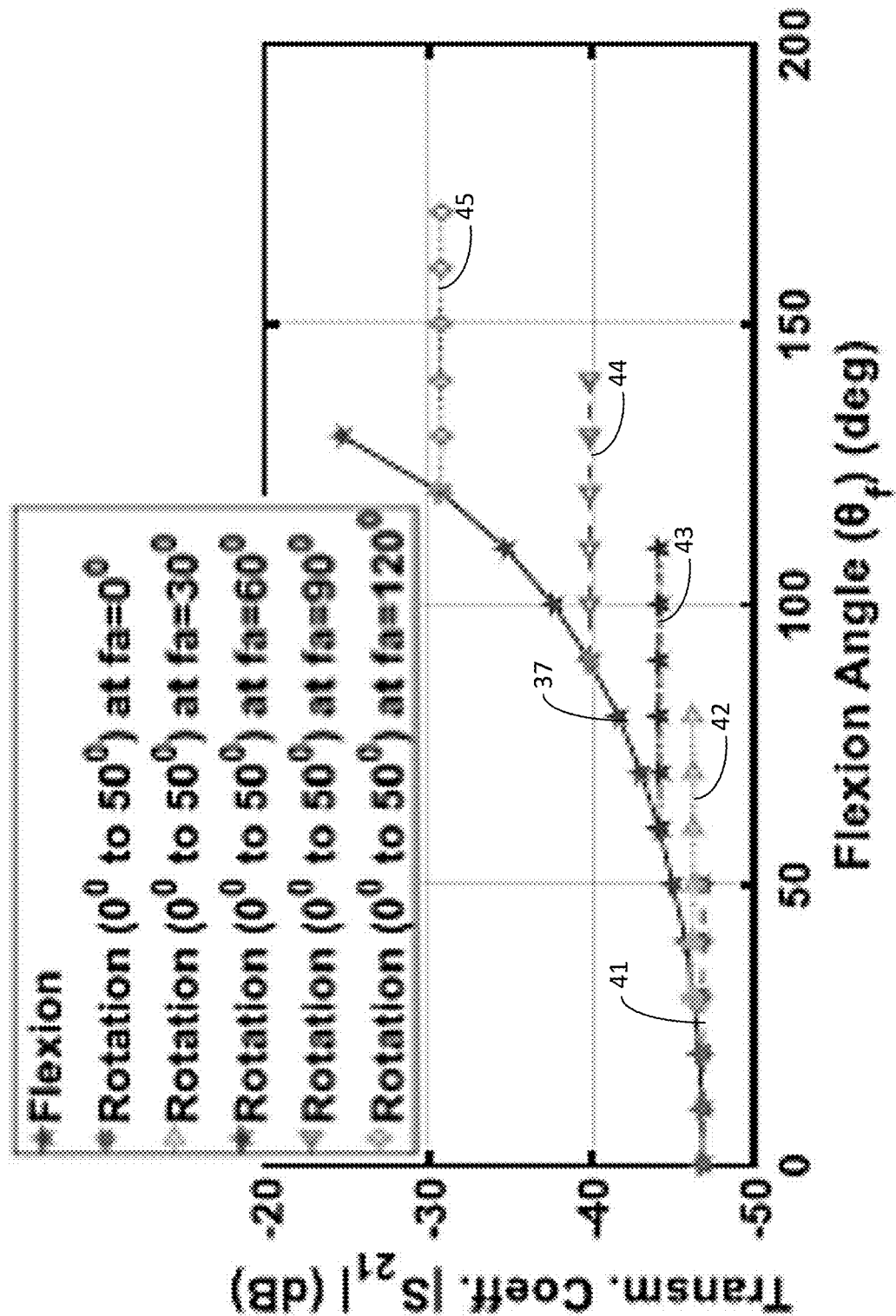
FIG. 11 is a plot of transmission coefficient $|S_{21}|$ as a function of flexion angle.

Limb rotation about its own axis (e.g., forearm pronation and supination), should not impact the flexion angle measurements. To validate the latter, rotation of the forearm about its own axis (from 0° to 50°) is included in the model of FIGS. 2A and 2B. Simulation results are summarized in FIG. 11. FIG. 11 is a plot of transmission coefficient $|S_{21}|$ as a function of flexion angle shown in solid curve 37. Dotted curves 41, 42, 43, 44 and 45 correspond to $|S_{21}|$ as a function of rotation angle at flexion angle $\theta_f$=0°, 30°, 60°, 90°, and 120°, respectively. The results highlight system robustness to limb rotation. Here, the solid curve plots $|S_{21}|$ as a function of flexion angle ($\theta_f$), while the dotted curves plot $|S_{21}|$ as the forearm rotates at given flexion angles ($\theta_f$=0°, 30°, 60°, 90°, and 120°). Remarkably, the captured $|S_{21}|$ value at any given flexion angle is not impacted by limb rotation. This is attributed to the inherent symmetry of the wrap-around coils, i.e., limb rotation does not change the flux linkage as there is no relative change in the area vector. Overall, this is one of the unique advantages of the joint flexion monitoring system disclosed herein that makes it extremely robust to rotation.

D. Multi-Coil Configurations

Referring again to the real-world application shown in FIG. 1, a scenario can be considered where the Tx or Rx coil breaks down; the whole system will stop operating. Alternatively, consider an unforeseen scenario where error creeps in the measurement of the induced voltage at the Rx coil (e.g., Rx coil unwillingly shifts upon the garment); the measured flexion angles will be erroneous. To overcome such problems and increase system reliability/robustness, multi-coil configurations can be pursued. By adding multiple Tx and/or Rx coils, there is always a back-up in case of failure, while additional S-parameter data points are brought into play to statistically improve the measurement accuracy.

Figure 12:
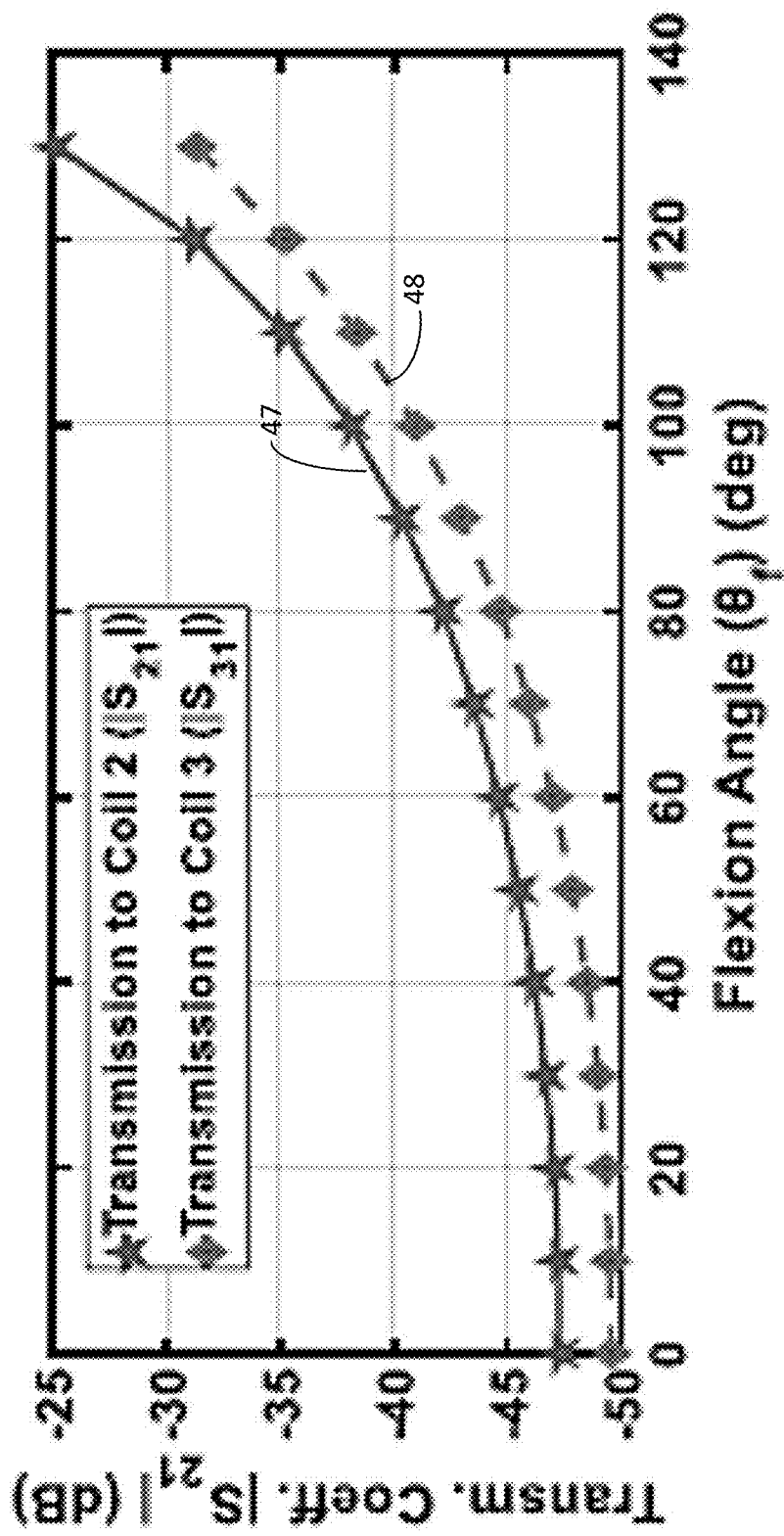
FIG. 12 is a plot of the transmission coefficient values $|S_{21}|$ and $|S_{31}|$ as a function of flexion angle; curve 47 is the plot of the transmission coefficient values $|S_{21}|$ as a function of flexion angle and curve 48 is the plot of the transmission coefficient values $|S_{31}|$ as a function of flexion angle.

To demonstrate, the three-coil setup shown in FIG. 2 is employed, where coil 1a is transmitting and coils 1b and 1c are receiving. In this example, $g_{12}$=20 cm and $g_{23}$=2 cm, per FIGS. 2A and 2B. Two sets of transmission coefficient values are recorded in this case, viz. $|S_{21}|$ and $|S_{31}|$, plotted in FIG. 12. FIG. 12 is a plot of the transmission coefficient values $|S_{21}|$ and $|S_{31}|$ as a function of flexion angle. Curve 47 is the plot of the transmission coefficient values $|S_{21}|$ as a function of flexion angle and curve 48 is the plot of the transmission coefficient values $|S_{31}|$ as a function of flexion angle. As seen in FIG. 12, each of the Rx coils 1b and 1c can independently monitor flexion. Of course, more Tx and/or Rx coils can be added, per application requirements.

E. Specific Absorption Rate

To ensure conformance with international safety guidelines, Specific Absorption Rate (SAR) studies are performed. To do so, the cylindrical arm model of FIGS. 2A and 2B is considered, yet with a more realistic multi-tissue configuration. Specifically, skin, fat, muscle, cortical bone, and bone marrow tissues are employed, with thicknesses equal to, 1.17 mm, 6.63 mm, 21.45 mm, 4.68 mm and 5.07 mm, respectively. Thickness of the layers is obtained using the ratio calculated from a known multi-layered model. Mass density values for each tissue are obtained, as is known in the art, and input power is set to −15 dBm (31.62 µW), as used to perform the experiments in Section V. In this case, the maximum SAR value calculated over 1 g of tissue is equal to 3.98 µW/Kg, which is far less than the 1.6 W/kg maximum level allowed by the Federal Communications Commission (FCC). In fact, to hit the aforementioned FCC limit, the input power of the system disclosed herein may be as high as 12.7 W. That is, the design is safe for human use.

VII. Conclusion Regarding Transverse Coil System Configuration

A new approach was described above with reference to FIGS. 1-12 for seamlessly monitoring joint flexion using wrap-around coils, while being insensitive to relative rotation of the limb. Proof-of-concept simulation results were presented, validated by in vitro measurements, and further supplemented by discussions on design guidelines and safety considerations. Contrary to state-of-the-art technologies used to monitor joint flexion, the system and method disclosed here: a) can be seamlessly integrated into garments for real-world monitoring, b) do not suffer from integration errors, c) do not require line-of-sight, and d) do not obstruct natural joint movement. Concurrently, the system and method are extremely robust to inter-/intra-subject variability, and bring forward multiple degrees of freedom to optimize the design, per application requirements.

While single-turn wrap-around coils are used in the experimental setup described above, multi-turn configurations may also be used, as will be understood by persons of skill in the art. Once fully optimized, this technology is envisioned to be employed as stand-alone and/or in combination with state-of-the-art technologies toward applications as diverse as rehabilitation, virtual reality, sports, and so on. The inventive principles and concepts are not limited with respect to the applications in which they may be employed, as will be understood by persons of skill in the art.

Having described examples of transverse coil configurations, examples of longitudinal coil configurations will now be described. In the following, electrically small loop antennas (ESLAs) that are placed longitudinally upon the limbs (i.e., plane of the ESLA is parallel to the axis of the limb to monitor motion while being robust to tissue variations and overcoming shortcomings in the state-of-the-art. Notably, the ESLAs are capable of operating in real-time, are capable of being made seamless, do not obstruct natural movement, and may operate in the individual's natural environment. The system and method significantly can outperform the transverse wrap-around coil configurations described above in that they: (a) can monitor both joint flexion and rotation, (b) are not dependent on the limb geometry (enabling sensor interoperability among different subjects and/or different joints), and (c) exhibit remarkable improvement in flexion angle resolution. For an example configuration of 10 cm distance between the ESLAs, the transmission coefficient range for 0° to 100° flexion can improve by 18.8 dB compared to the transverse coil configurations described above with reference to FIGS. 1-12. Concurrently, lower flexion angles that can be detected at 0.1 dB sensitivity improve by 6.7 times (1.5° vs. 10°).

In the following, systems and methods are described in which ESLAs are secured longitudinally across the joint to seamlessly monitor flexion and rotation. A two-ESLA system configuration is discussed first, illuminating the merit of the idea, yet indicating ambiguities under combined flexion and rotation scenarios for angular resolutions higher than 10°. To tackle this, a three-ESLA system configuration with integrated post-processing is proposed, offering a resolution of 2° for combined flexion and rotation monitoring. Simulation results are presented and further validated by in vitro experiments. Guidelines for system design suited to diverse applications are discussed, followed by studies that explore conformance to electromagnetic safety standards for the SAR.

VIII. Operating Principle Regarding Longitudinal Coil System Configurations

Figure 13:
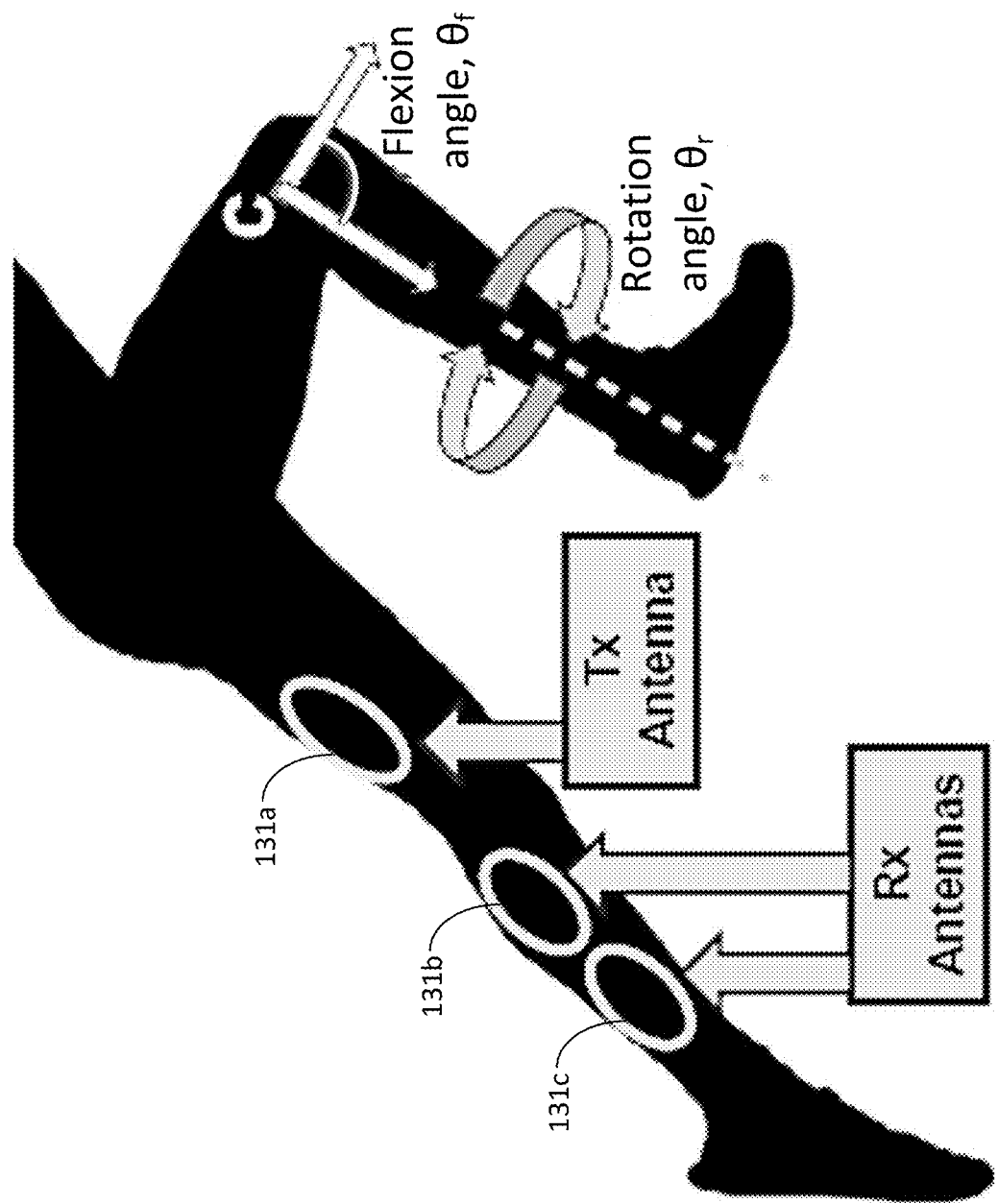
FIG. 13 shows a silhouette of a person running who has a longitudinal coil system configuration secured to his or her leg in accordance with a representative embodiment.

FIG. 13 shows a silhouette of a person running who has a longitudinal coil system configuration secured to his or her leg in accordance with a representative embodiment. As shown in FIG. 13, the Tx and Rx ESLA coils are placed on opposite side of the joint. Though focus of the examples below is on the knee joint, the method and system is readily applicable to other joints as well.

Figures 14A, 14B:
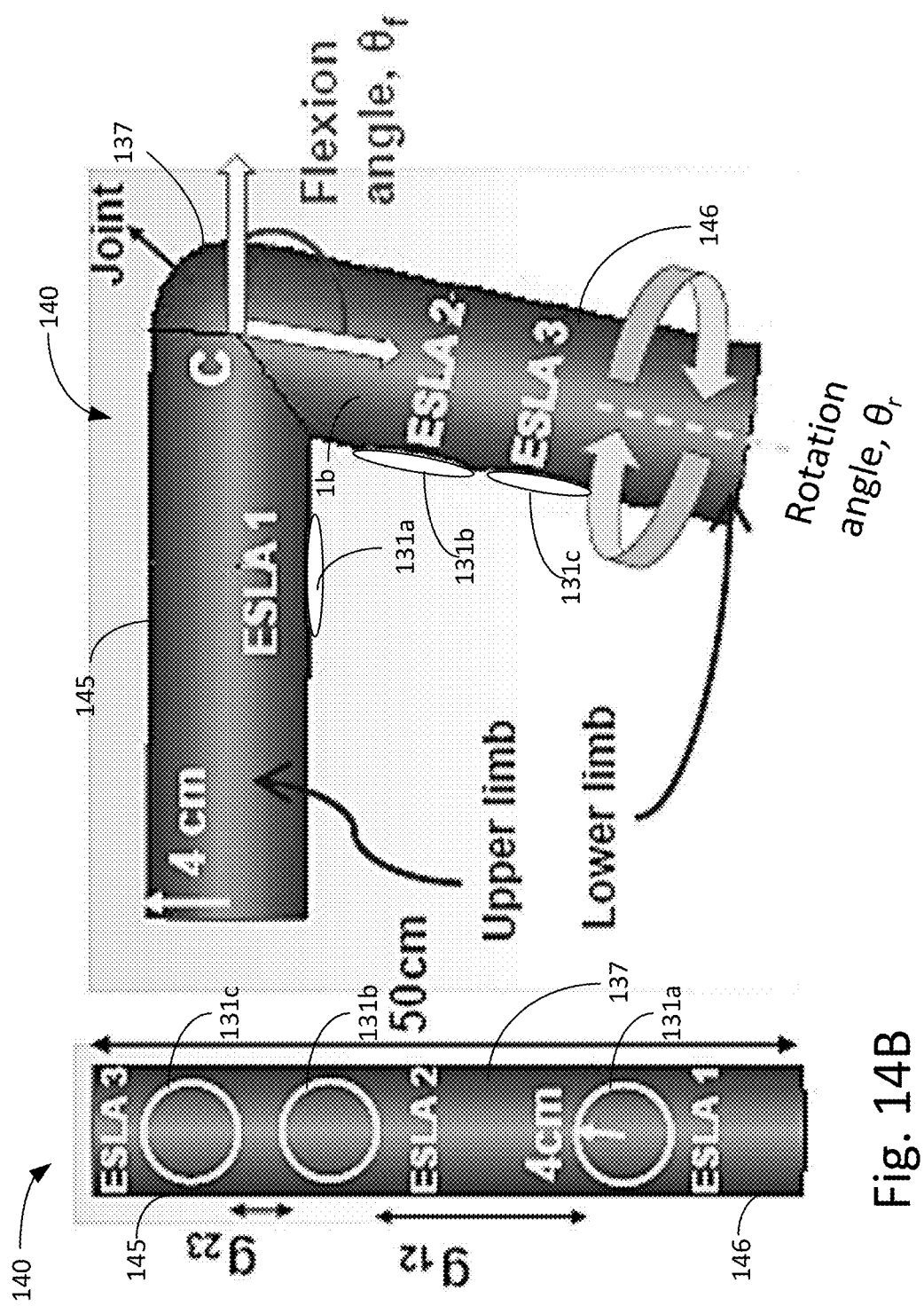
FIGS. 14A and 14B show side and top views, respectively, of a simulation setup for the longitudinal coil configuration of a wearable system in accordance with a representative embodiment secured to a homogeneous cylindrical model having a portion representing the upper limb of a human leg and a portion representing the lower limb of the human leg.

FIGS. 14A and 14B show side and top views, respectively, of a simulation setup for the longitudinal coil configuration of a wearable system in accordance with a representative embodiment secured to a homogeneous cylindrical model 140 having a portion 145 representing the upper limb of a human leg and a portion 146 representing the lower limb of the human leg. Longitudinal ESLA coil 131a acts as a transmitter while longitudinal ESLA coils 131b and 131c act as receiver coils. The upper limb 145 and the lower limb 146 are modeled as cylinders (3.9 cm in radius, 25 cm in length), while the knee joint 137 is modeled as a sphere (3.9 cm in radius). The tissue-simulating material is ⅔ muscle, as frequently used in the art to represent the average human body properties.

Flexion is achieved when the lower limb 146 rotates with respect to the upper limb about the center 'C' of the joint 137. At full extension (FIG. 14B), the limbs 145 and 146 are straight and the flexion angle is zero, $\theta_f=0°$. As the lower limb 146 flexes about the joint, flexion angle $\theta_f$ increases. Similarly, the lower limb 146 may also rotate (by angle $\theta_r$) about the joint 137. In both flexion and rotation scenarios, the Tx ESLA coil 131a and the Rx ESLA coil 131b become misaligned, leading to changes in the associated transmission coefficient(s). In turn, such changes can be monitored to identify the exact flexion or/and rotation angles.

In principle, the system of FIGS. 14A and 14B can be realized using three modes of operation, viz. (a) electrically large loops (circumference~$\lambda$, where $\lambda$ represents wavelength), (b) electrically small loops (circumference<0.1$\lambda$), or (c) in between both modes of operation (0.1$\lambda$<circumference<$\lambda$). Extensive frequency studies indicate that ESLAs operating at 34 MHz provide optimal performance in terms of: a) received power levels, b) resolution (smallest detectable angle), and c) robustness to changes in tissue properties.

The operating principle is based on Faraday's law given above in Equation (1). Changes in flexion/rotation angle are reflected in $V_{Rx}$, and eventually captured in the transmission coefficient. That is, transmission coefficient becomes a function of flexion/rotation angle and hence can be used to monitor joint flexion and rotation.

As will be shown next, one transmitter and one receiver are enough to monitor joint flexion (at a given $\theta_r$) or rotation (at a given $\theta_f$). However, monitoring both flexion and rotation via a single transmitter/receiver pair leads to ambiguities for applications that require resolution higher than 10°. In other words, the same values of the transmission coefficient will end up corresponding to several different states of motion. To resolve ambiguities, two receiver antennas can be used. As such, Section IX focuses on a two-ESLA configuration that will be used as a building block towards a three-ESLA configuration in Section X.

IX. Two-ESLA Configuration

A. Simulations

In the simulation setup 140 shown in FIGS. 14A and 14B, ESLA coil 131a serves as Tx and ESLA coil 131b serves as Rx. A homogenous (⅔ of muscle properties) cylindrical model is used as a first order approximation to human limbs, while the joint 137 is modeled as a sphere. For this proof-of-concept model, the limb, joint and ESLA radius are set to 4 cm. Copper wire is used to realize the ESLA coils 131a and 131b (0.254 mm diameter), and a lumped capacitor (102 pF) is loaded on each of the ESLA coils to introduce resonance and improve performance. The gap, $g_{12}$, between the ESLA coils 131a and 131b in the extended state is set to 10 cm, in turn enabling flexion in the 0° to 100° range. Flexion ($\theta_f=0°$ to 100°) and rotation ($\theta_r=0°$ to 50°) are then incorporated in the model. For simulations, the frequency domain solver of CST Microwave Studio® (based on Finite Integral Technique) is used with tetrahedral meshing.

Figure 15:
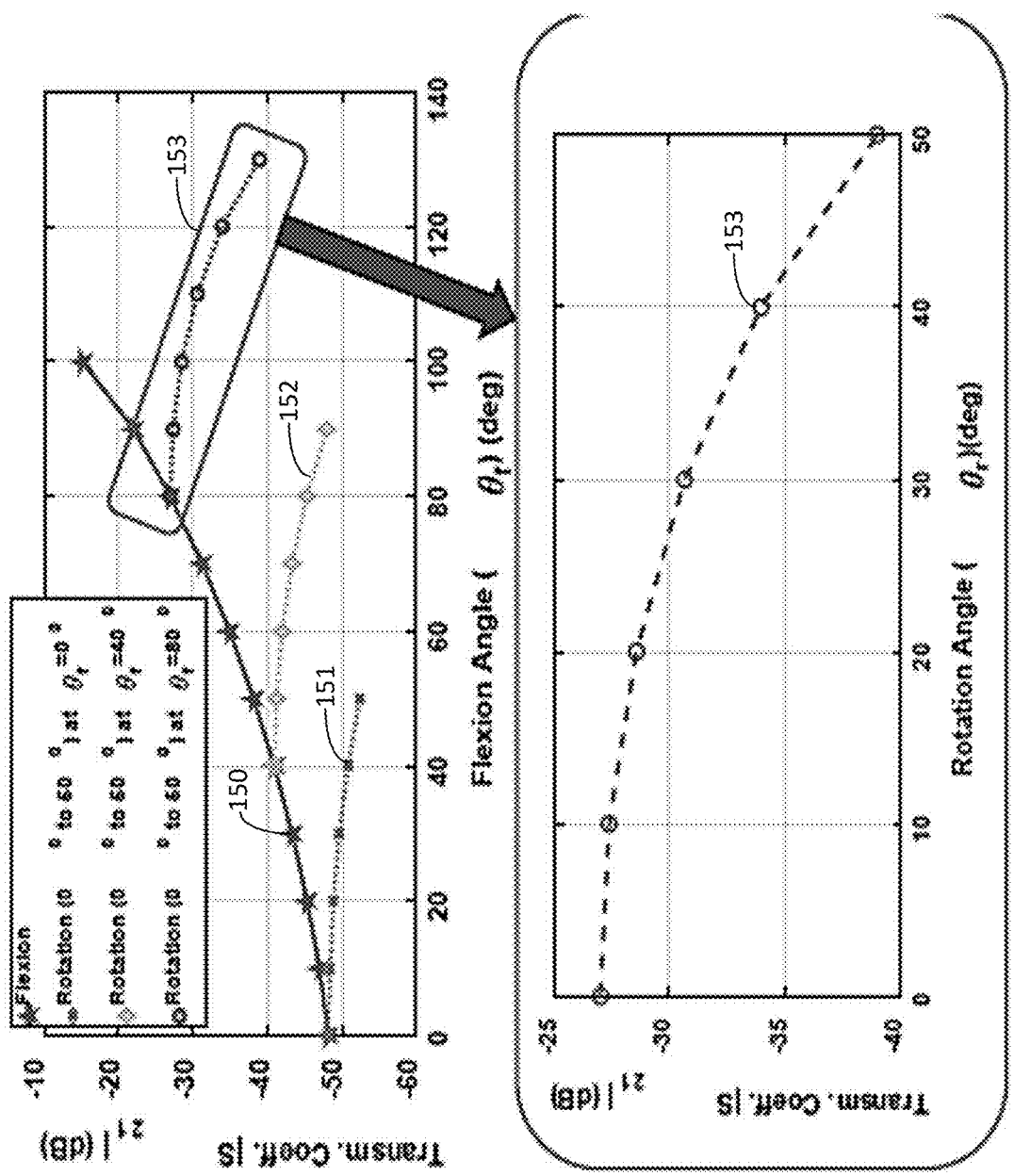
FIG. 15 is a plot depicting changes in the simulated transmission coefficient values ($|S_{21}|$) with varying flexion angle and rotation angle at 34 MHz; the bottom inset depicts an example rotation curve 153 at $\theta_f = 80°$.

FIG. 15 is a plot depicting changes in the simulated transmission coefficient values ($|S_{21}|$) with varying flexion angle and rotation angle at 34 MHz. The bottom inset depicts an example rotation curve 153 at $\theta_f=80°$. Simulated transmission coefficients ($|S_{21}|$) at the resonance frequency of 34 MHz are shown in FIG. 15. To provide a complete picture, FIG. 15 shows plots indicative rotation curves 151, 152 and 153 for $\theta_r=0°$, 40° and 80°, respectively, along with indicative flexion curve 150 ($\theta_f=0°$ to 100°, at 10° steps). In this case, each rotation curve represents the change in $|S_{21}|$ as $\theta_r$ changes at a particular flexion angle. As an example, the rotation curve 153 at $\theta_f=80°$ is shown in the inset of FIG. 15. As expected, changes in flexion and/or rotation angle imply significant changes in $|S_{21}|$. In other words, $|S_{21}|$ can be monitored to assess joint flexion and rotation.

B. Experimental Validation

Figure 16A:
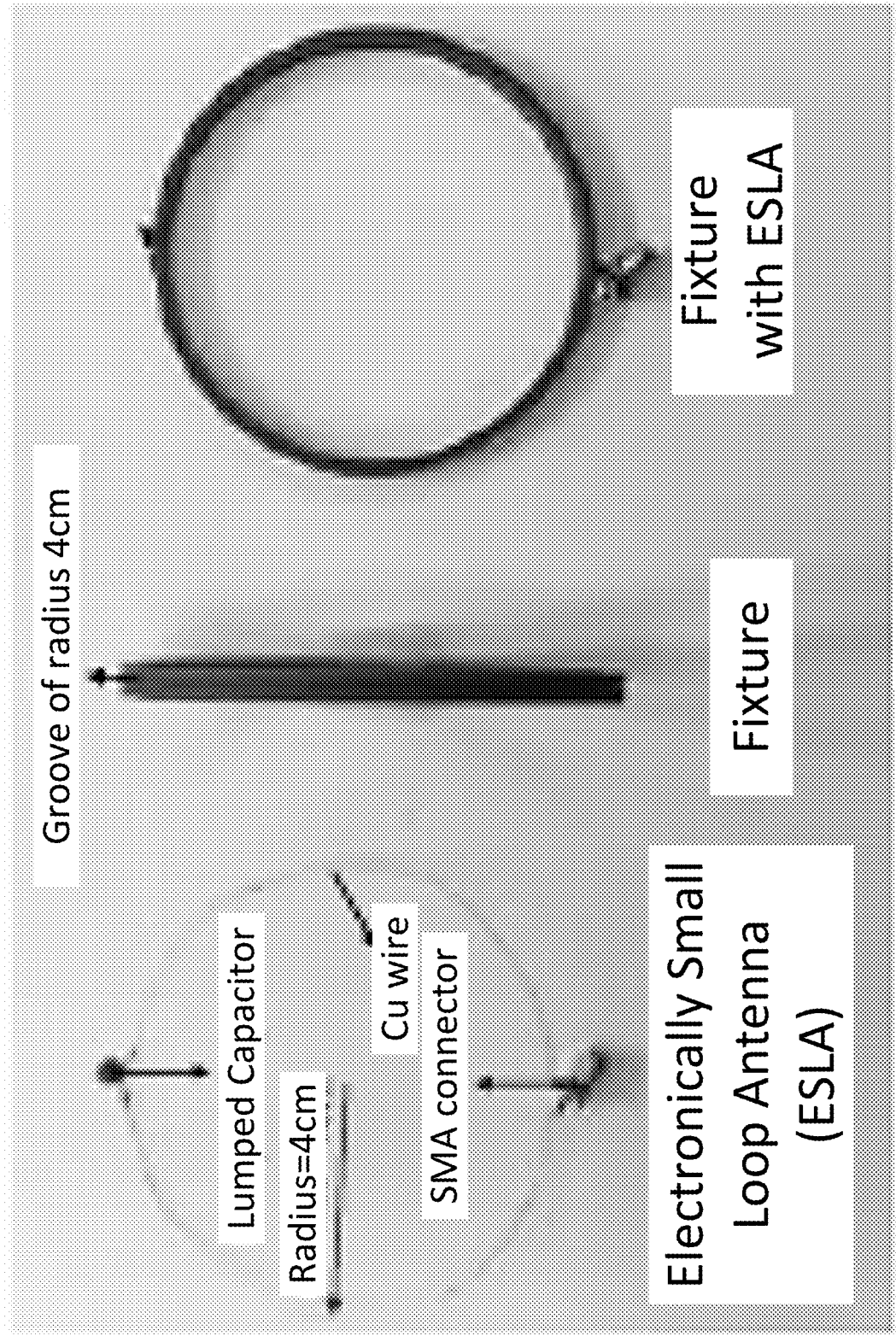
FIGS. 16A-16D show an experimental setup for the longitudinal coil system configuration.
Figure 16B:
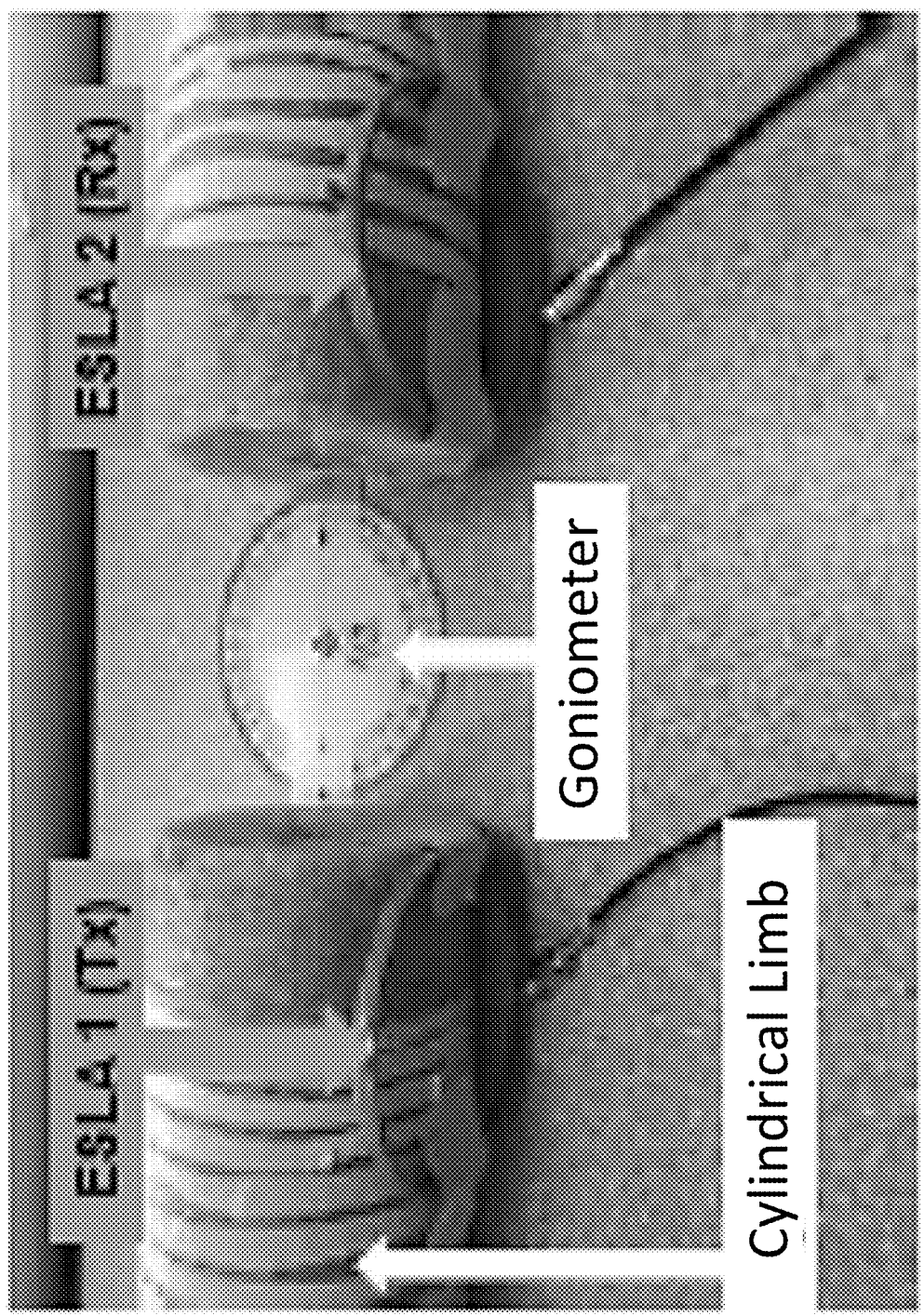
Figure 16C:
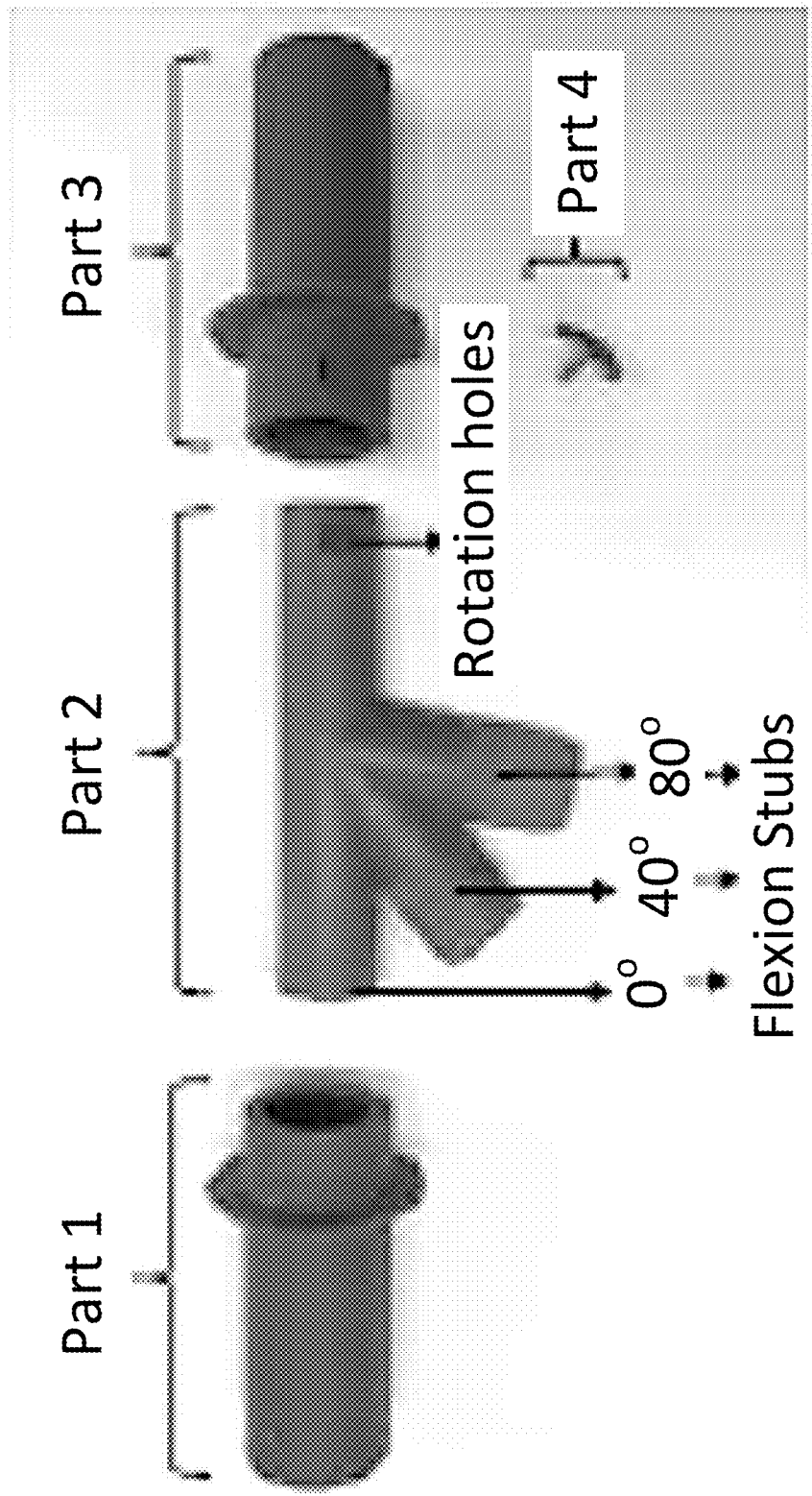
Figure 16D:
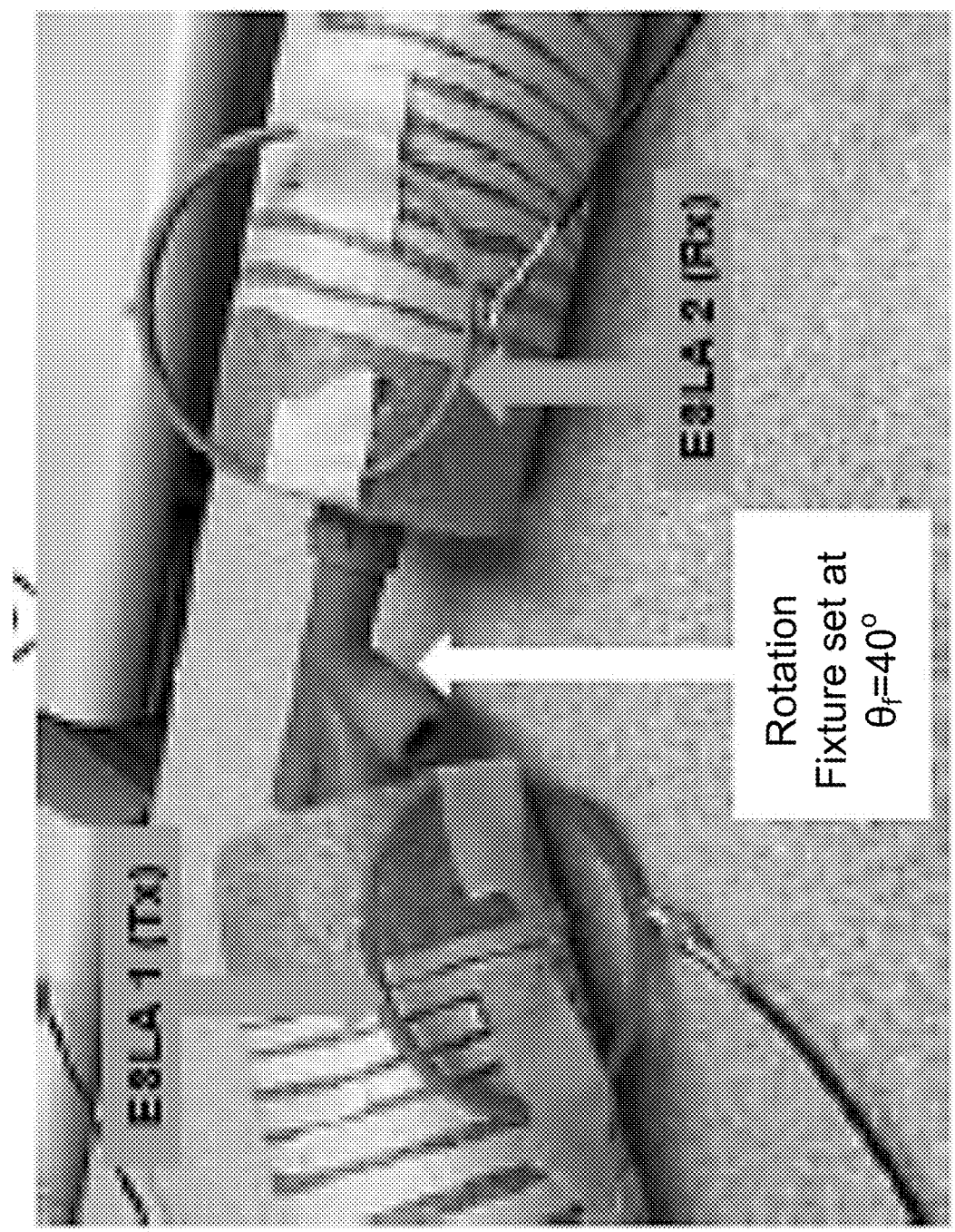

FIGS. 16A-16D show the experimental setup for the longitudinal ESLA coil system configuration. FIG. 16A shows the ESLA coil made of copper wire and subsequent integration in a 3D-printed fixture with a groove. FIG. 16B shows the flexion measurement setup with goniometer, Styrofoam limbs and ESLA coils connected to a network analyzer. FIG. 16C shows a fixture devised to enable controllable flexion and rotation (the four parts are eventually combined into one). FIG. 16D shows the combined flexion and rotation measurement setup ($\theta_f=40°$ and $\theta_r=50°$).

For the experimental setup, the ESLA coils of radius 4 cm are fabricated using 30 AWG (0.254 mm diameter) copper wire and are further soldered to 102 pF lumped capacitors and SMA connectors, as shown in FIG. 16A. To secure the coils, 3D-printed fixtures with a groove are used, as shown in FIG. 16A. The limb is realized using cylindrical Styrofoam of radius 4 cm, as enabled by the insensitivity of ESLAs coil' performance in presence or absence of tissues. The goniometer, commonly used to measure flexion angles in clinical practices, is inserted inside the upper/lower limbs, as shown in FIG. 16B. The goniometer serves to emulate the flexing portion of the hinge joint while also assisting in setting up the intended flexion angle.

To incorporate controllable rotation into the design, the fixture of FIG. 16C is devised and 3D-printed. The fixture has four parts: parts 1 and 3 are fixed in the upper and lower limbs, respectively; part 2 contains stubs for flexion at 0°, 40°, and 80° and holes for rotation from 0° to 50° at 10° steps; part 4 helps fix the desired rotation angle by aligning the rotation holes between part 2 and part 3. FIG. 16D depicts an example setup with combined flexion and rotation ($\theta_f=40°$ and $\theta_r=50°$). To align with simulations, the fixture is designed such that the gap $g_{12}$ between the Tx and Rx ESLA coils 131a and 131b, respectively, is maintained at 10 cm for all flexion angles. For both flexion and rotation measurements, the ESLA coils are connected to the two ports of a PNA-L N5235A network analyzer by Keysight Technologies.

Figure 17:
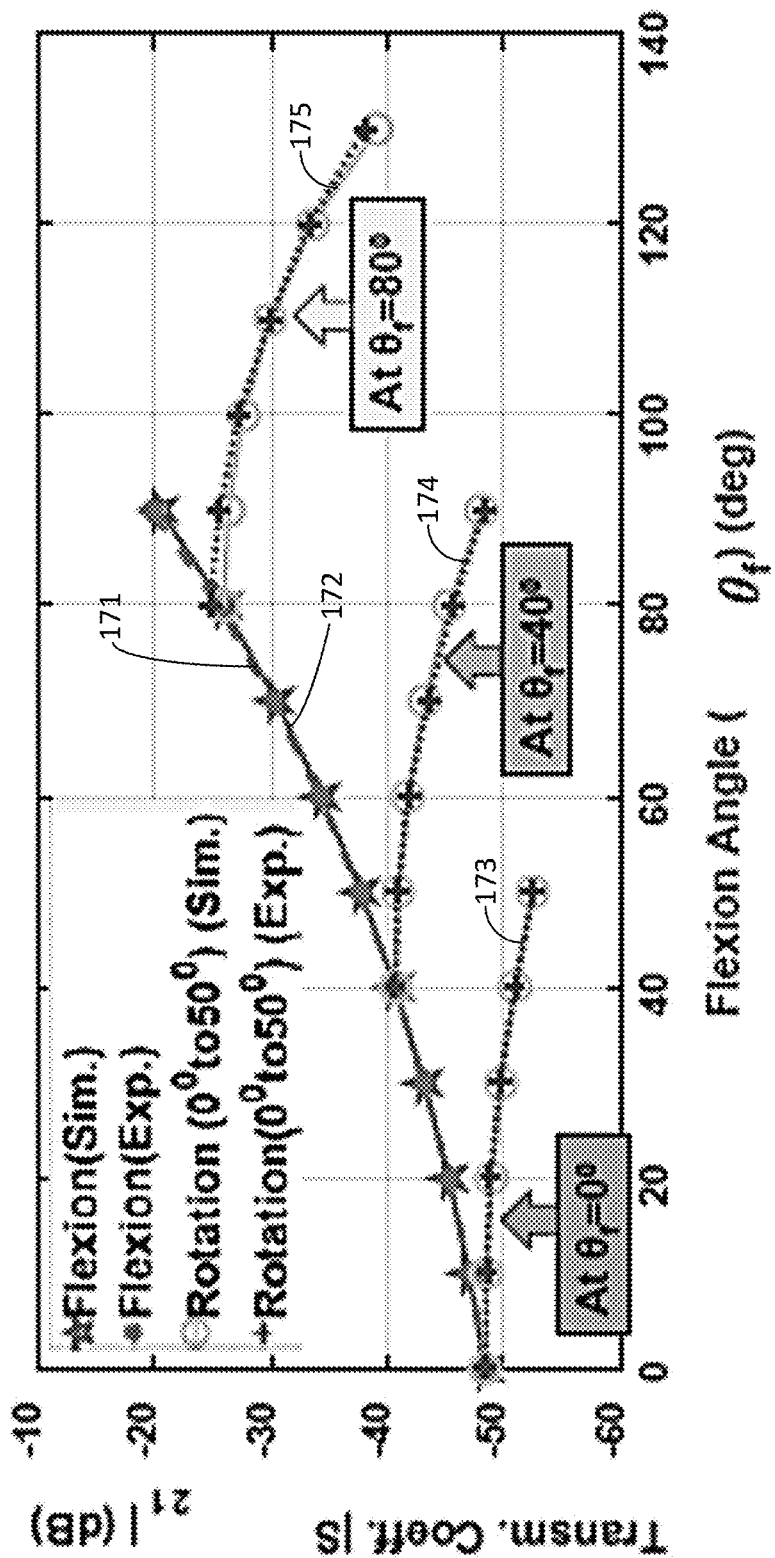
FIG. 17 is a plot of simulated and experimental results for transmission coefficient as a function of flexion angle and rotation angle for the longitudinal coil system configuration shown in FIGS. 16B and 16D.

Experimental results are shown in FIG. 17 and further superimposed with simulations. FIG. 17 is a plot of simulated and experimental results for transmission coefficient as a function of flexion angle and rotation angle. Curves 171 and 172, which are in complete agreement and overlap over their extents, correspond to the simulated and experimental results of the transmission coefficients, respectively, as a function of flexion angle. Curves 173, 174 and 175 correspond to transmission coefficient values as a function of rotation angle for $\theta_f=0°$, 40° and 80°, respectively. As seen in FIG. 17, excellent agreement is achieved, further validating the ESLA approach for monitoring flexion and rotation angles.

C. Ambiguity Considerations

As is clearly indicated in FIG. 17, there is no one-to-one correlation between measured $|S_{21}|$ and associated flexion/rotation angles. For example, assuming a measurement of $|S_{21}|=-30$ dB, it is possible that ($\theta_f=70°$, $\theta_r=0°$) or ($\theta_f=80°$, $\theta_r=30°$), among others. Nevertheless, and as will become clear in Section X.B, it is still possible to monitor both flexion and rotation using this configuration for applications that require resolution down to, for example, 10°. But for applications that require higher resolution, ambiguities arise in deciphering the correct position of the limb. To tackle this, a three-ESLA-coil configuration with integrated post-processing is discussed next. The results of FIG. 17 are, in turn, used as a building block toward the three-ESLA-coil design.

X. Three-ESLA-Coil System Configuration

A. Operating Principle

Using the three-ESLA-coil system configuration shown in FIGS. 14A and 14B, where ESLA coil 131a serves as Tx and ESLA coils 131b and 131c serve as Rxs, the same flexion and rotation angles are now captured by two different receivers. Notably, these receivers 131b and 131c are positioned asymmetrically with respect to the transmitter 131a, implying that asymmetric trends are anticipated in the $|S_{21}|$ and $|S_{31}|$ values. This is demonstrated below in Section X.B. In turn, ambiguous ($\theta_f, \theta_r$) pairs arising by the $|S_{21}|$ and $|S_{31}|$ curves will not be the same. Ideally, there should be only a single flexion/rotation angle combination that is identified by both $|S_{21}|$ and $|S_{31}|$ plots, and this will be the true and desired reading. This is discussed below in Section X.C.

B. Simulation and Experimental Results

Figure 18A:
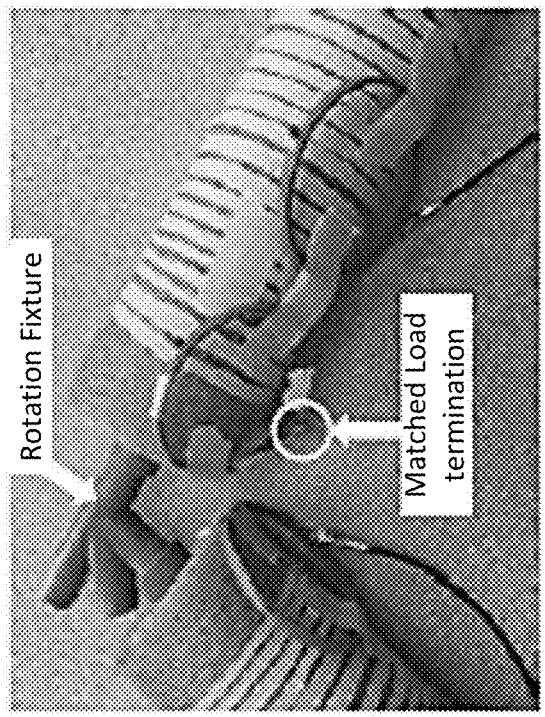
FIG. 18A shows the experimental setup for a longitudinal coil system configuration, where an inserted goniometer helps set the flexion angle.
Figure 18B:
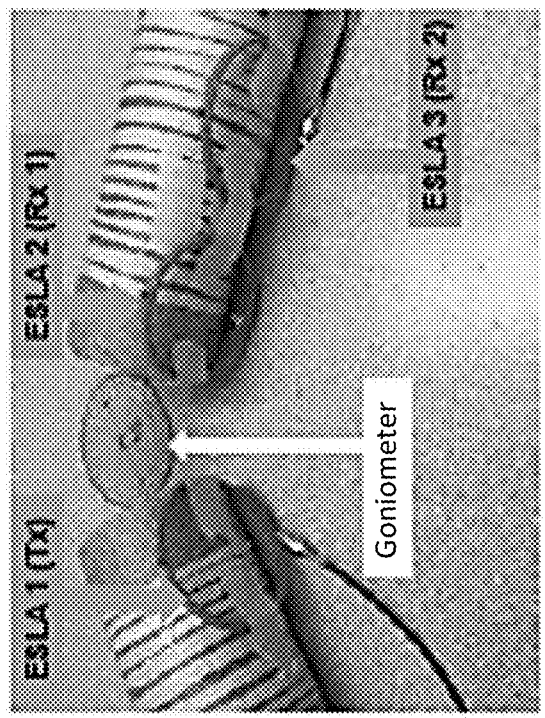
FIG. 18B shows the combined flexion/rotation-monitoring experimental setup that implements the 3D-printed fixture of FIG. 16C.
Figure 18C:
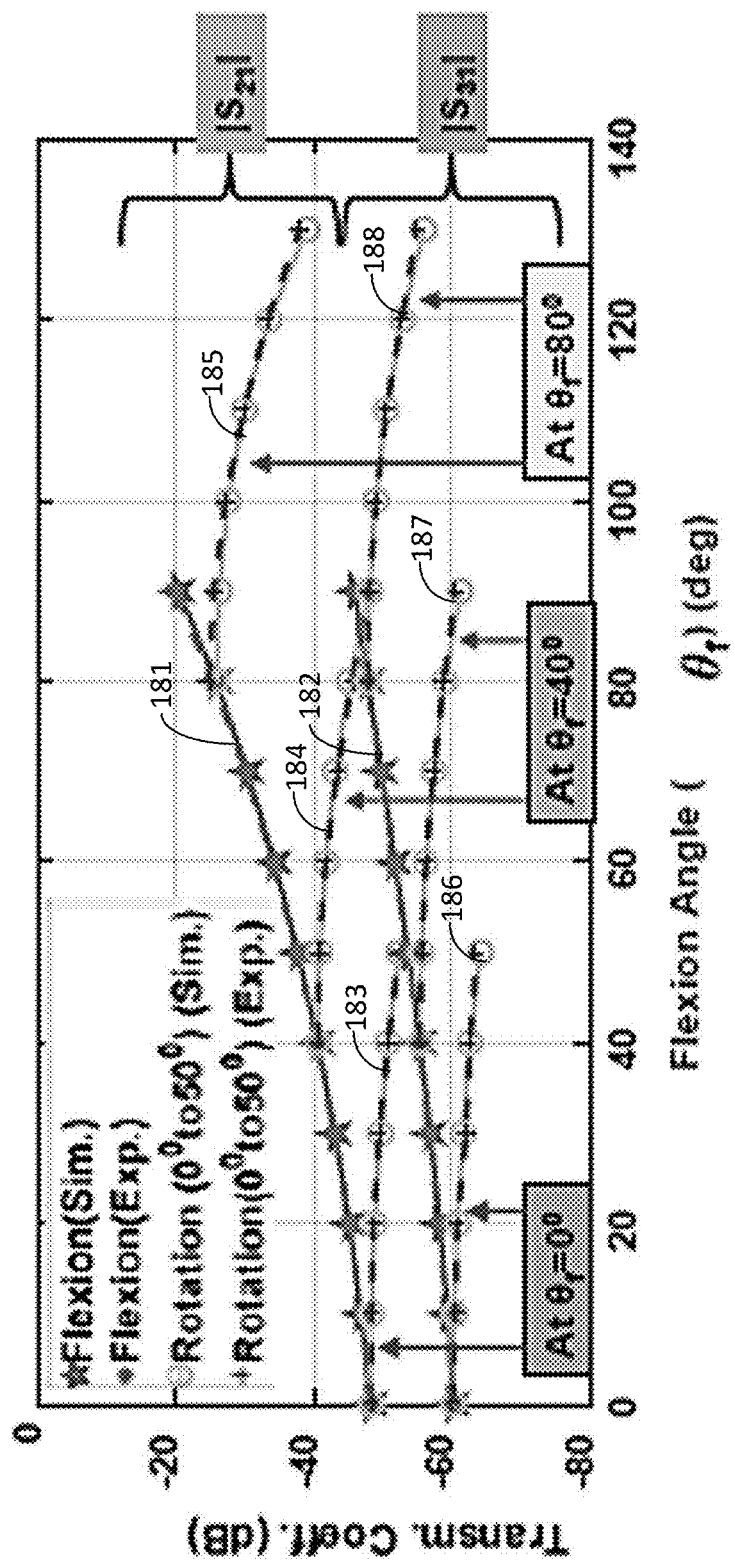
FIG. 18C shows the simulation and measurement results of transmission coefficient values as a function of flexion angle over a range or rotation angles for the simulation setup shown in FIGS. 14A and 14B and for the experimental setup shown in FIGS. 18A and 18B.

Simulations were performed using the three-ESLA-coil system configuration shown in FIGS. 14A and 14B. For the simulations, ESLA coils 131b and 131c are separated by a gap ($g_{23}$) of 2 cm while ESLA coils 131a and 131b are separated by a gap ($g_{12}$) of 10 cm. Simulations are carried out for $\theta_f=0°$ to 100° (at steps of 10°) and $\theta_r=0°$ to 50° (at steps of 10° and at $\theta_f=0°$, 40° and 80°). Corresponding experiments are performed on the Styrofoam phantom shown in FIGS. 16B and 16D. For flexion-only monitoring, the employed setup is shown in FIG. 18A, where an inserted goniometer helps set the flexion angle. For combined flexion/rotation-monitoring, the 3D-printed fixture of FIG. 16C is employed, as shown in FIG. 18B. Transmission coefficient values are measured using a two-port network analyzer, one receiver at a time. While taking $|S_{21}|$ measurements, ESLA 131c is terminated with a 50Ω load, and vice versa. This accounts for practical scenarios where both receivers are connected to 50Ω rather than being left open. FIG. 18C shows the simulation and measurement results of transmission coefficient values as a function of flexion angle over a range or rotation angles. Curve 181 corresponds to the simulation and experimental results of the transmission coefficient values $|S_{21}|$ as a function of flexion angles ranging from 0° to 90° for the three-ESLA-coil system configuration. Curve 182 corresponds to simulation and experimental results of the transmission coefficient values $|S_{31}|$ as a function of flexion angles ranging from 0° to 90° for the three-ESLA-coil system configuration. The simulation and experimental results depicted in FIG. 18C are in excellent agreement. Curves 183, 184 and 185 correspond to the transmission coefficient values $|S_{21}|$ as a function of rotation angles for flexion angles of 0°, 40° and 80°, respectively. Curves 186, 187 and 188 correspond to the transmission coefficient values $|S_{31}|$ as a function of rotation angles for flexion angles of 0°, 40° and 80°, respectively.

C. Resolving Ambiguities

To evaluate the feasibility of resolving ambiguities, simulations are carried out for $\theta_f=0°$ to 100° (at 10° steps) and $\theta_r=0°$ to 50° (at 10° steps, and at $\theta_f=0°$ to 100° at 10° steps). The step size of 10° throughout these simulations sets the system resolution to 10° and leads to a total of 132 data points (i.e., $|S_{21}|$ and $|S_{31}|$ values). With precision set to two decimal digits, post-processing is performed in Matlab® to identify ambiguities in $|S_{21}|$ and $|S_{31}|$, and resolve them as needed. For a system resolution of 10°, no ambiguities are identified, implying that just a two-ESLA configuration is sufficient in this case. For a system resolution of lower than 10°, similar behavior is expected.

Similar tests are subsequently performed at higher system resolutions, as shown below in Table I. As expected, ambiguities arise for both $|S_{21}|$ and $|S_{31}|$, with the number of ambiguities increasing at higher resolutions. Notably, no overlap is found in the ambiguities of $|S_{21}|$ vs. the ambiguities of $|S_{31}|$ for resolutions as high as 2°. That is, the three-ESLA-coil system configuration is able to resolve ambiguities within a system resolution of as high as 2°. For resolutions higher than 2°, ambiguities cannot be resolved (Table I). This can be surmounted by: (a) using more than two Rx coils, or (b) judiciously selecting the ESLA radius and gap ($g_{12}$), both of which play a crucial role in controlling the resolution per Section IX. Of course, the aforementioned results are tied to the two decimal precision selected above. The number of ambiguous ($\theta_f, \theta_r$) pairs is anticipated to decrease with higher precision.

TABLE I

POST-PROCESSING FOR DIFFERENT
ANGULAR RESOLUTIONS

| Resolution | Total Data Points | Number of Ambiguities $|S_{21}|$ | Number of Ambiguities $|S_{31}|$ | Ambiguity Overlaps |
|---|---|---|---|---|
| 10° | 132 | 0 | 0 | 0 |
| 5° | 462 | 1 | 1 | 0 |
| 3.3° | 992 | 3 | 3 | 0 |
| 2.5° | 1722 | 13 | 15 | 0 |
| 2° | 2652 | 25 | 21 | 0 |
| 1.67° | 3782 | 29 | 54 | 1 |
| 1.43° | 5112 | 53 | 75 | 1 |
| 1.25 | 6642 | 88 | 137 | 1 |
| 1.11° | 8372 | 109 | 221 | 5 |
| 1° | 10302 | 179 | 252 | 10 |

TABLE II

COMPARISON OF DYNAMIC RANGE

| | | $|S_{21}|$ Dynamic Range (dB) | | |
|---|---|---|---|---|
| $g_{12}$ (cm) | $\theta_f$ (deg) | [22] | This work | Improvement |
| 20 | 0° to 130° | 22.1 | 44.6 | 22.5 |
| | 0° to 60° | 2.62 | 10.43 | 7.81 |
| | 0° to 20° | 0.16 | 2.16 | 2 |
| 10 | 0° to 100° | 14.24 | 33.03 | 18.79 |
| | 0° to 60° | 3.26 | 13.23 | 9.97 |
| | 0° to 20° | 0.36 | 2.86 | 2.5 |
| 5 | 0° to 60° | 6.2 | 19.92 | 13.72 |
| | 0° to 20° | 0.46 | 4.2 | 3.74 |
| 2 | 0° to 20° | 1.24 | 7.26 | 6.02 |
| | 0° to 5° | 0.07 | 1.44 | 1.37 |
| 0.5 | 0° to 5° | 0.4 | 3.19 | 2.75 |
| | 0° to 1° | 0.01 | 0.52 | 0.51 |
| | 0° to 0.1° | — | 0.04 | — |

XI. Performance Metrics

Key performance metrics are hereafter identified and analyzed, aiming to serve as guidelines for system design suited to diverse applications now and in the future. For simplicity purposes, the two-ESLA-coil system configuration is considered first, followed by discussions on applicability to the three-ESLA system.

A. Resolution

Resolution is governed by the dynamic range of transmission coefficient values across a desired range of flexion/rotation angles. Higher dynamic ranges lead to finer discrimination of angular values, hence improving resolution. Of course, this is valid only because the transmission coefficient curves are monotonically increasing/decreasing functions. Note that, dynamic range and resolution are not completely analogous here, as the slope is not constant throughout. However, since the slope does not change drastically, it does provide a good measure as a first order approximation for quantification and comparison purposes.

As seen in FIG. 17, the slope of the flexion/rotation curves at lower angles is lower as compared to higher angles. This reduces the dynamic range and, hence, the resolution at lower angles. Added to the above, this reduced dynamic range increases the chances of ($\theta_f$, $\theta_r$) ambiguities at lower angles and, in turn, increases the difficulty in resolving them. In fact, for all resolution tests performed beyond 2°, all overlaps occur at $\theta_f$<30°. Nevertheless, fine-tuning of $g_{12}$, ESLA radius, and/or operation frequency may control/improve resolution, as outlined below.

1) Fine-Tuning the ESLA Gap

Figure 19A:
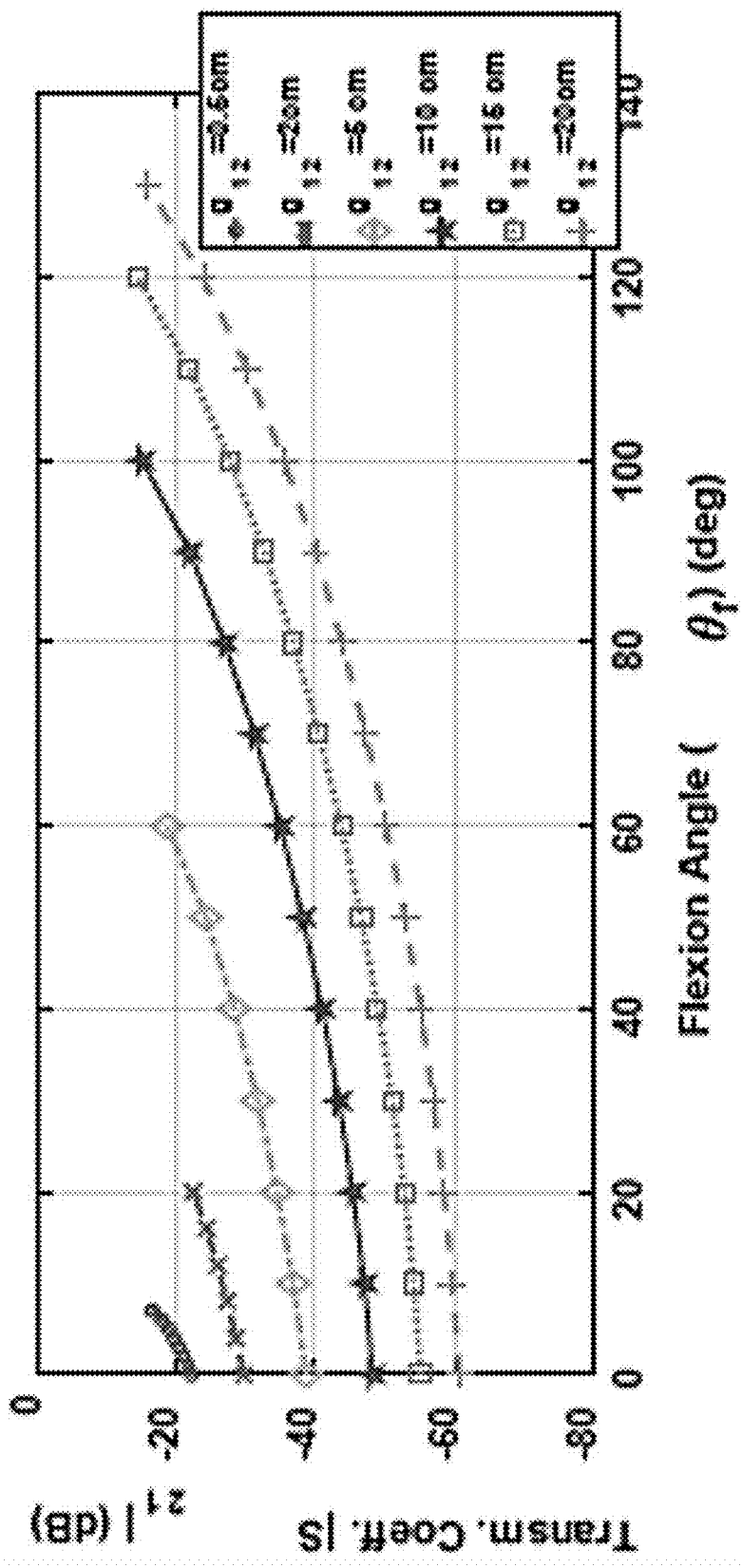
FIG. 19A is a plot of a flexion curve for different values of gaps ($g_{12}$) between first and second longitudinal coils.
Figure 19B:
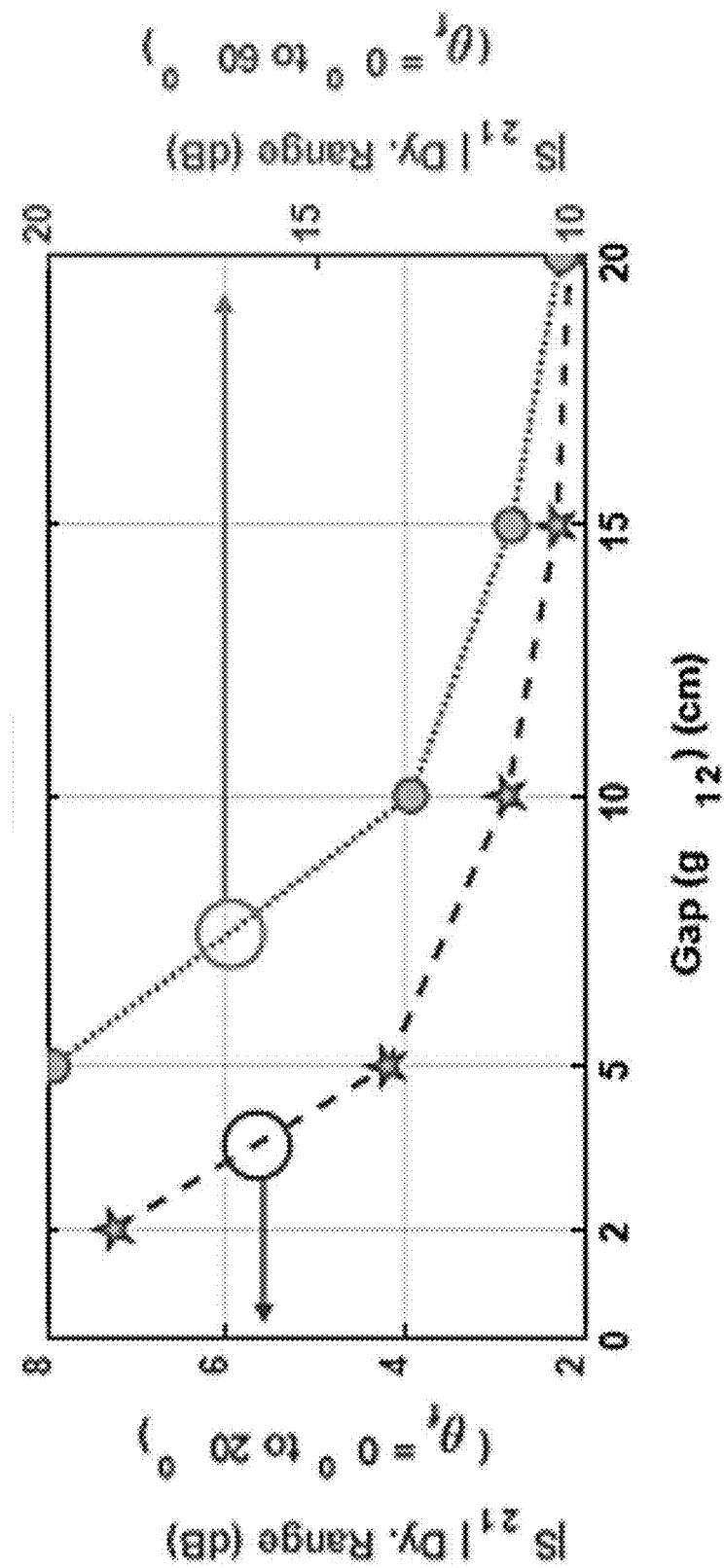
FIG. 19B is a plot of the increase in dynamic range for both $\theta_f = 0°$ to 20° and $\theta_f = 0°$ to 60° with decrease in $g_{12}$.

FIG. 19A is a plot of a flexion curve for different values of gaps ($g_{12}$) between the first and second ESLA coils 131a and 131b. FIG. 19B is a plot of the increase in dynamic range for both $\theta_f$=0° to 20° and $\theta_f$=0° to 60° with decrease in $g_{12}$. Considering $g_{12}$ as the design parameter, and for flexion only scenario ($\theta_r$=0°), FIG. 19A plots flexion curves ($|S_{21}|$ vs. $\theta_f$) for different values of gaps ($g_{12}$). As seen, the slope or dynamic range improves with decreasing $g_{12}$. To better visualize this, FIG. 19B plots the $|S_{21}|$ dynamic range (across $\theta_f$=0° to 60° and $\theta_f$=0° to 20°) as a function of $g_{12}$. Indeed, the dynamic range improves significantly with decrease in $g_{12}$ even at smaller angles. Quantitative results are shown in Table II and are further compared vs. those of previously discussed for the wrap-around coils. As seen, significant improvement is achieved.

Figure 20A:
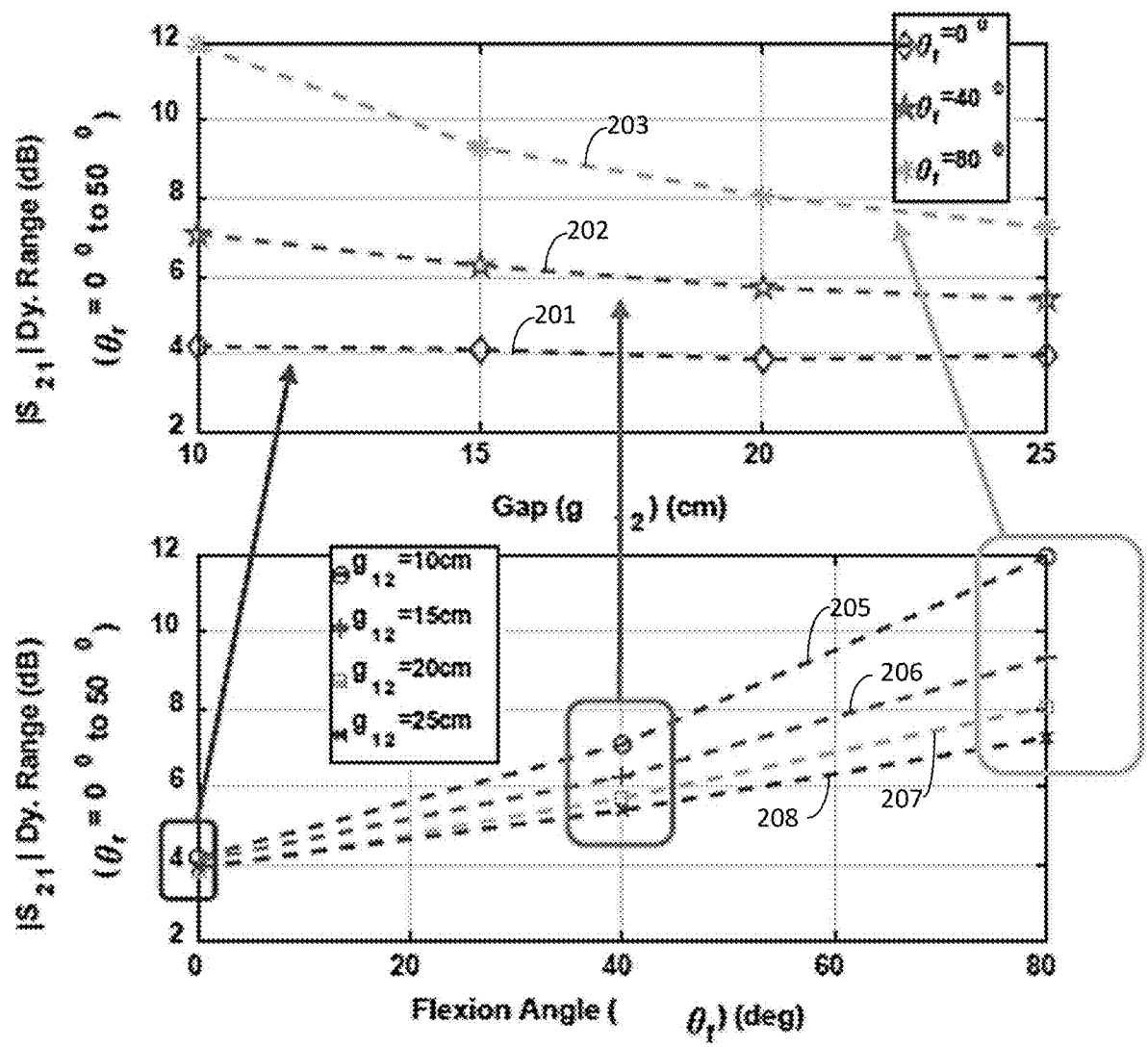
FIG. 20A is a plot of the dynamic range $|S_{21}|$ variation for rotation ($\theta r = 0°$ to 50°) with $\theta_f$ for different values of gap ($g_{12}$), and, with gap ($g_{12}$) for different values of $\theta_f$.
Figure 20B:
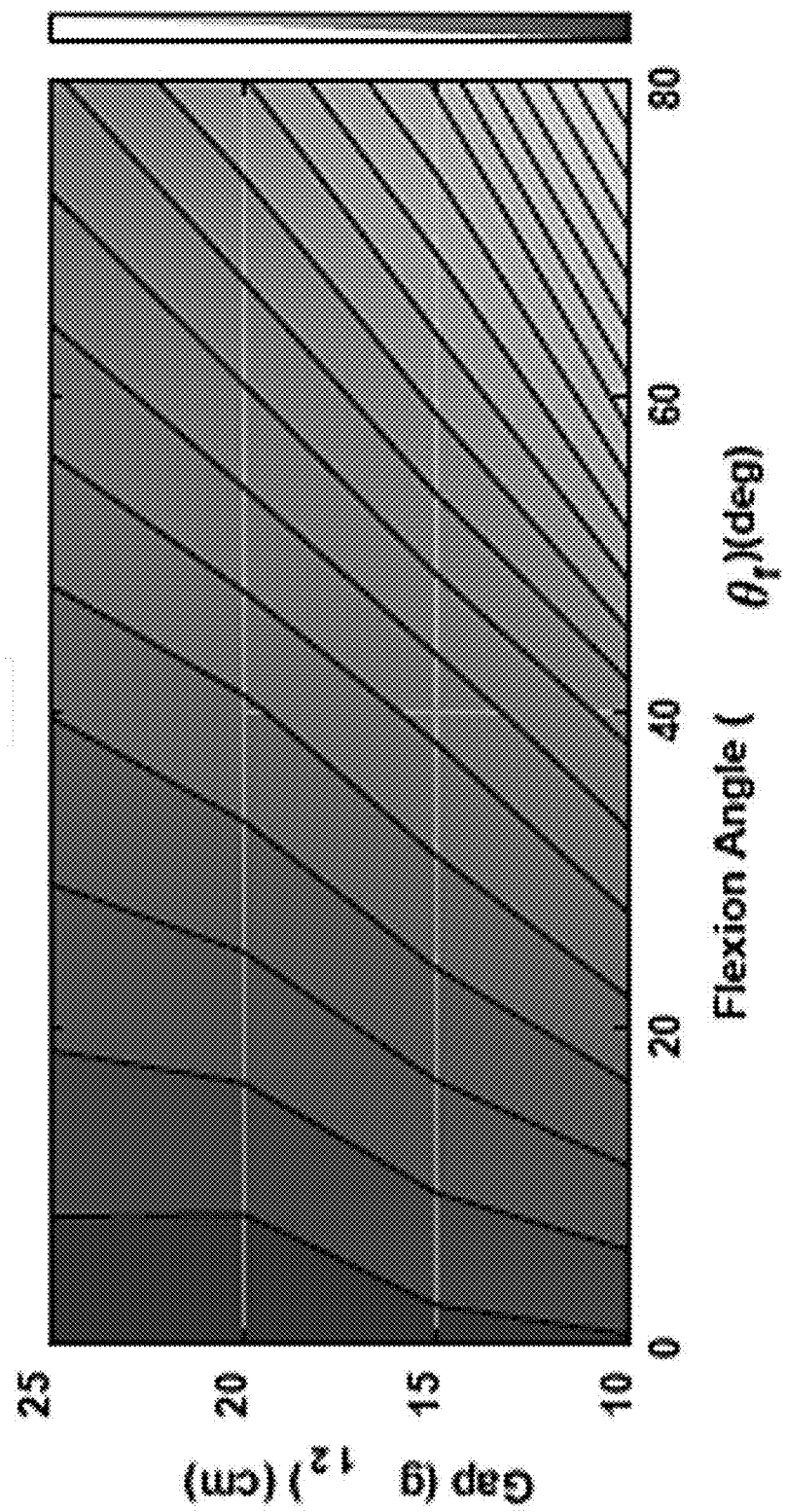
FIG. 20B is a contour plot simultaneously depicting the variation with both $g_{12}$ and $\theta_f$ depicted in FIG. 20A.

FIG. 20A is a plot of the dynamic range $|S_{21}|$ variation for rotation ($\theta_r$=0° to 50°) with $\theta_f$ for different values of gap ($g_{12}$), and, with gap ($g_{12}$) for different values of $\theta_f$. FIG. 20B is a contour plot simultaneously depicting the variation with both $g_{12}$ and $\theta_f$ depicted in FIG. 20A. Better range is obtained for smaller $g_{12}$ and larger $\theta_f$. For rotation, FIG. 20A (top) depicts the dynamic range variation vs. $g_{12}$ at different $\theta_f$ (curves 201, 202 and 203 corresponding to flexion angles 0, 40 and 80, respectively). FIG. 20A (bottom) depicts the dynamic range variation vs. $\theta_f$ at different $g_{12}$ (curves 205, 206, 207 and 208 corresponding to $g_{12}$ sizes of 10 cm, 15 cm, 20 cm and 25 cm, respectively). At high $\theta_f$, a decrease in $g_{12}$ helps improve the dynamic range (regardless of $\theta_r$), but is not very useful at smaller $\theta_f$. Also, it can be inferred from this that dynamic range for rotation is a function of both $g_{12}$ and $\theta_f$. Hence, FIG. 20B shows the intuitive effect of both parameters, depicting better dynamic range/resolution at higher $\theta_f$ and smaller $g_{12}$.

Following these guidelines, resolution of the three-ESLA-coil system configuration of FIGS. 14A and 14B may increase to 0.4° for $g_{12}$=3 cm as compared to 2° for $g_{12}$=10 cm. Thus, using $g_{12}$ as a design parameter, resolution of the complete system can be tweaked as needed or desired.

2) Fine-Tuning the ESLA Radius

Figure 21A:
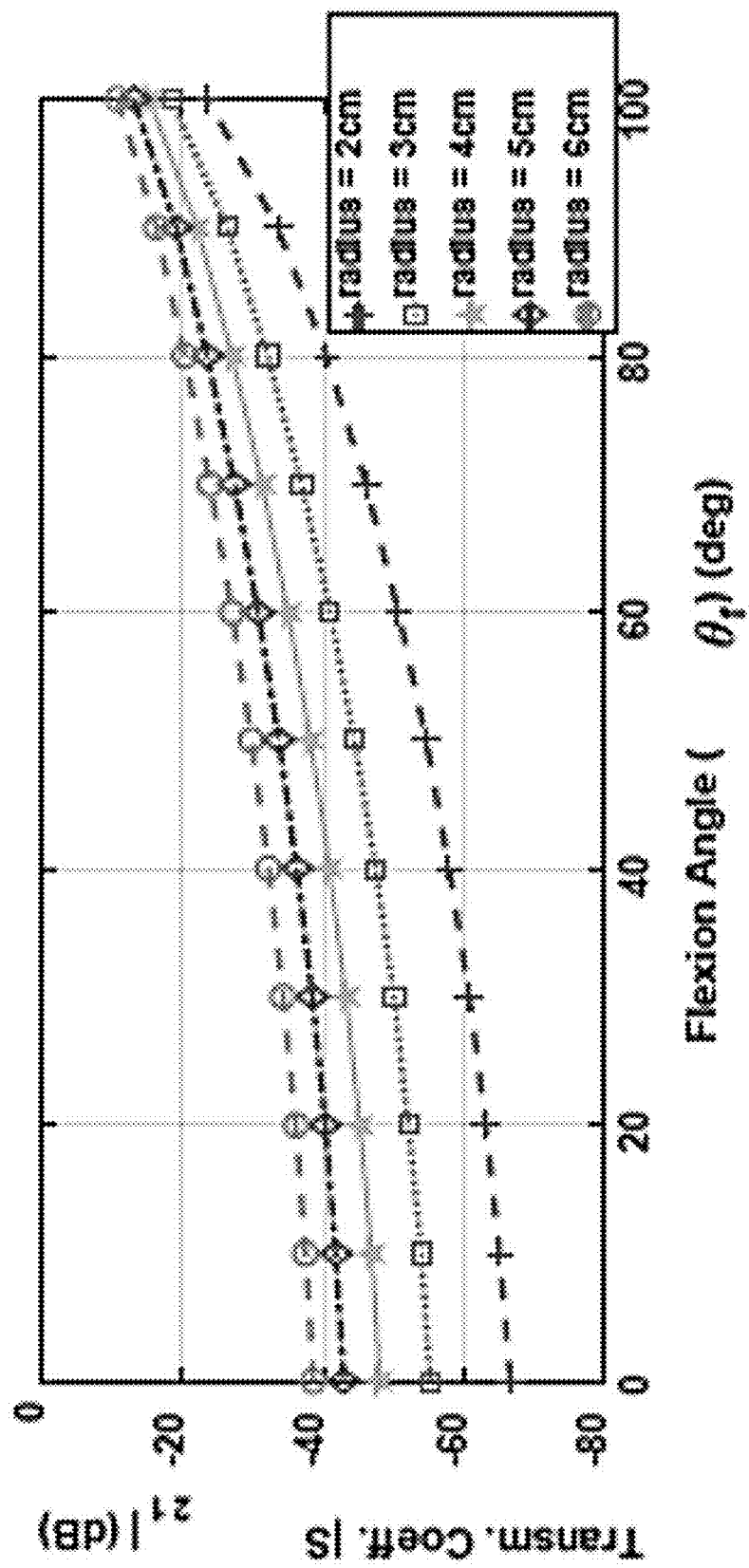
FIG. 21A plots flexion curves for longitudinal coils having different radii.
Figure 21B:
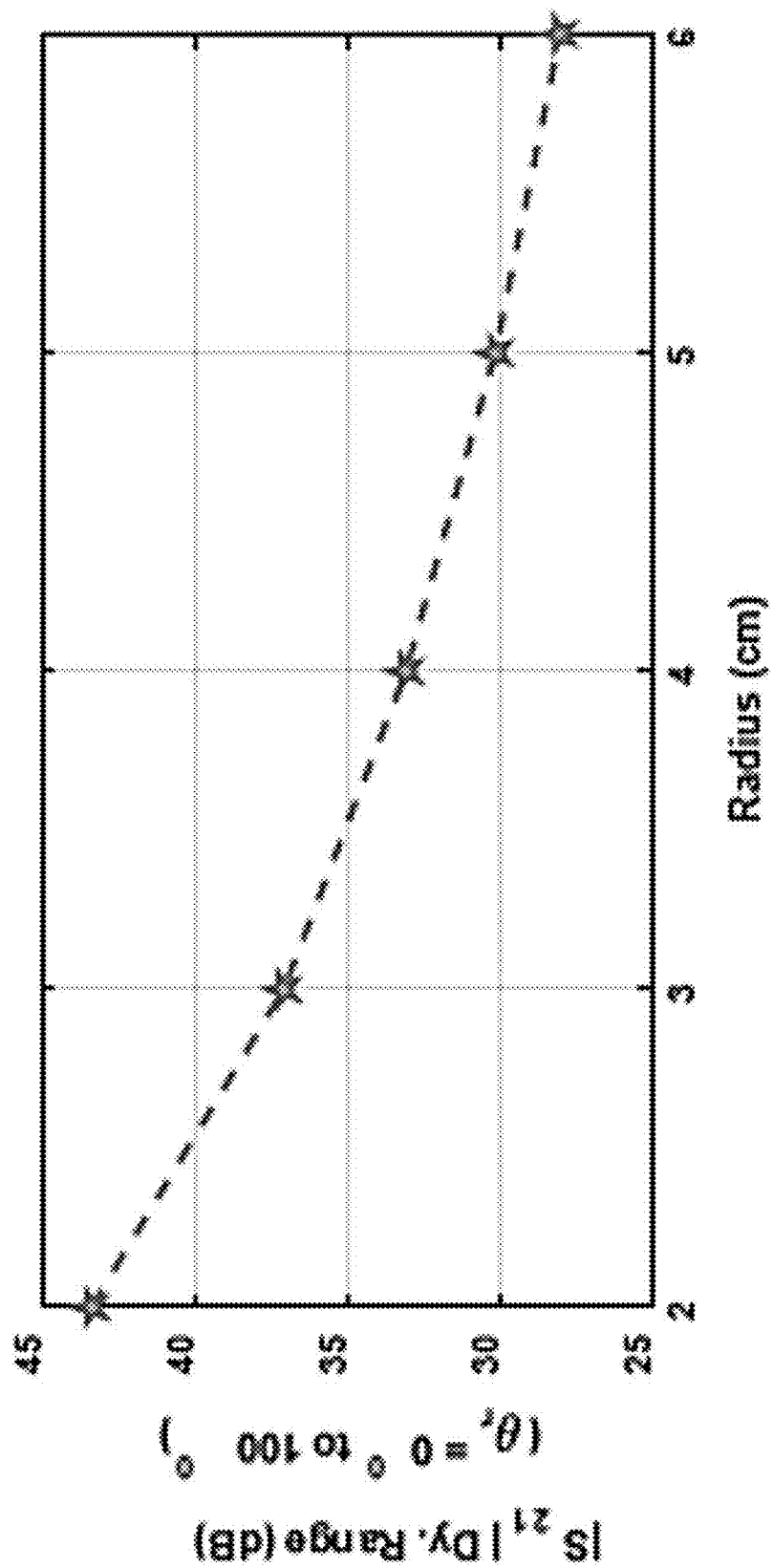
FIG. 21B plots the dynamic range for the plots shown in FIG. 21A

Assuming a flexion only scenario ($\theta r$=0°), FIG. 21A plots flexion curves for different ESLA radii, while FIG. 21B plots the corresponding dynamic range. As seen, a decrease in radius leads to better dynamic range for all $\theta_f$ values.

Figure 22A:
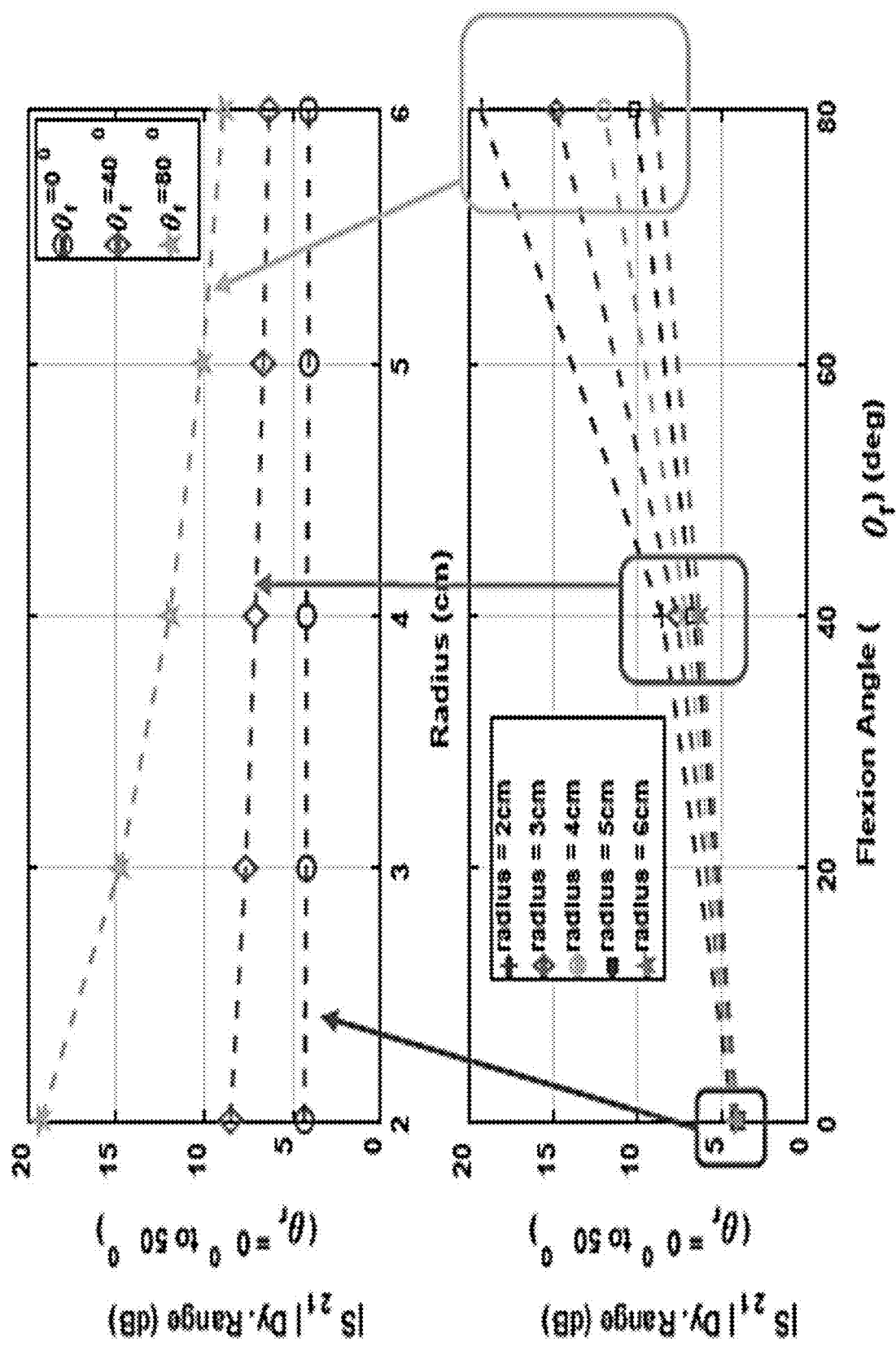
FIG. 22A is a plot of the variation in the dynamic range of the transmission coefficient $|S_{21}|$ for longitudinal coils for rotation ($\theta_r = 0°$ to 50°) with $\theta_f$ for different values of radius and with radius for different values of $\theta_f$.
Figure 22B:
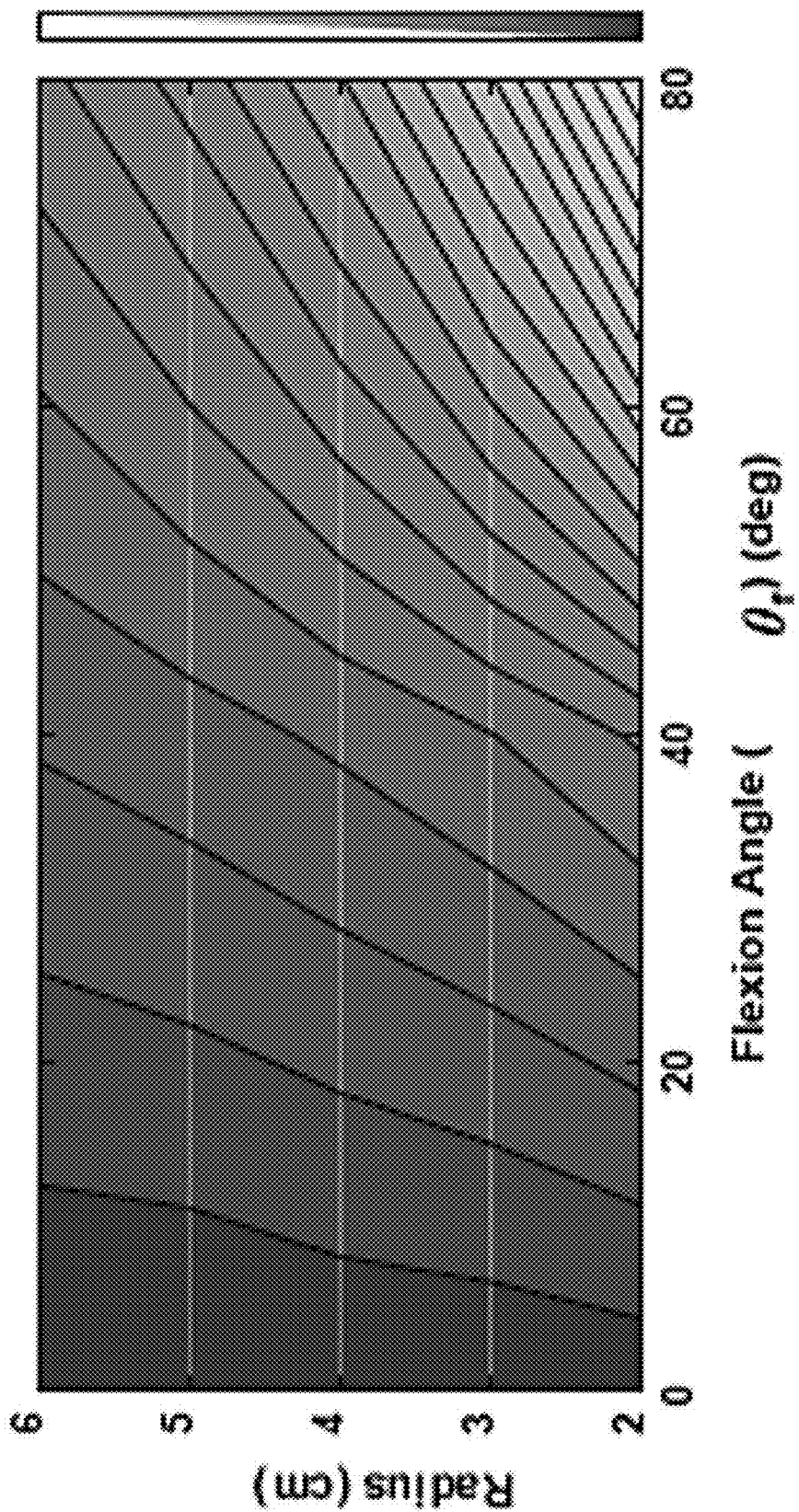
FIG. 22B is a contour plot depicting the variation of the transmission coefficient $|S_{21}|$ shown in the plot of FIG. 22A with both radius and $\theta_f$ simultaneously.

For rotation, radius variations depict very similar trends as those of $g_{12}$ variations, as shown in FIGS. 22A and 22B. FIG. 22A is a plot of the variation in the dynamic range of the transmission coefficient $|S_{21}|$ for rotation ($\theta r$=0° to 50°) with $\theta_f$ for different values of radius and with radius for different values of $\theta_f$. FIG. 22B is a contour plot depicting the variation with both radius and $\theta_f$ simultaneously. Better range is obtained for smaller radius and larger flexion angles. That is, better rotation resolution can be achieved at higher $\theta_f$ and at smaller radius values. The reason for this similar trend can be attributed to the fact that in both cases reduction in $g_{12}$ or radius leads to more drastic changes in flux linkage with angular variation.

Similar to $g_{12}$, radius reduction will also help improve the resolution of the three-ESLA-coil system configuration represented by the plots of FIGS. 22A and 22B. Since the effect of both parameters is similar, analyses performed for $g_{12}$ are not shown to avoid redundancy.

3) Fine-Tuning the Frequency

Considering frequency as a design parameter, lower frequency of operation leads to better flexion resolution. This is also one of the reasons behind the selection of 34 MHz as the optimal operating frequency. However, frequency selection has relatively negligible effect on the rotation resolution.

B. Range of Motion and Power Reception

Range of motion (ROM) relates to the range of flexion ($\theta_f$) and/or rotation ($\theta_r$) angles. Ideally, higher range of motion is desirable. With the present longitudinal configuration of two and three ESLA coils, there is no limit on the rotation ROM irrespective of $g_{12}$, radius, or $\theta_f$ variation. However, decrease in $g_{12}$ leads to reduction in flexion ROM as depicted in FIG. 19(a). This is because reduction in $g_{12}$ results in transmit and receive ESLA coils physically touching each other. Radius variation, on other hand, does not restrict flexion ROM, as depicted in FIG. 21A.

Power levels received by the Rx ESLA(s) are desired to be as high as possible. As is evident from FIGS. 19A and 21A, power reception improves with decrease in $g_{12}$ and increase in radius, respectively. Similar trends are observed for the rotation curves as well.

In a nutshell, by decreasing $g_{12}$, power reception and resolution increase, but ROM decreases. By decreasing the ESLA coil radius, power reception reduces, resolution increases, and ROM remains unaffected. These imply a trade-off in the design, a conclusion which is equally valid for the three-ESLA-coil system.

C. Insensitivity to Tissue Variation

System performance should be independent of tissue variations. An analysis similar to that performed above for the transverse coil configurations has been repeated for the proposed ESLA coil configurations, indicating that frequencies in the inductive region are again suitable to meet this requirement. This is yet another reason for the choice of 34 MHz as the optimal operating frequency.

D. Specific Absorption Rate Studies

To ensure conformance with international safety guidelines, SAR studies are performed. The multi-layer arm model discussed above is employed, consisting of 1.17 mm thick skin, 6.63 mm thick fat, 21.45 mm thick muscle, 4.68 mm thick cortical bone and 5.07 mm bone. For the two-ESLA-coil and three-ESLA-coil system configurations, and assuming an input power of −15 dBm (as used in the experiments), maximum SAR averaged over 1 g of tissue is equal to 1.44 μW/Kg. This value is extremely low as compared to the safety limit of 1.6 W/Kg set by the FCC.

XII. Conclusion Regarding the Longitudinal ESLA Coil System Configurations

A unique configuration of wearable longitudinal ESLA coils was disclosed for seamlessly monitoring joint flexion and rotation. The longitudinal ESLA-coil system configuration and method (a) have the potential to break lab boundaries and enable monitoring in the individual's natural environment, (b) are not restricted by line-of-sight concerns (unlike optical cameras and time-of-flight sensors), (c) do not restrict natural motion (unlike bending sensors), (d) do not drift (unlike IMUs), and (e) can monitor both flexion and rotation.

A two-ESLA-coil system configuration was reported first, able to monitor flexion and rotation at resolutions of 10° or lower. However, ambiguities were shown to arise for applications that require higher resolution. To tackle this, a three-ESLA-coil system configuration with accompanying post-processing was reported, achieving resolution of as high as 2° at an example distance of 10 cm between the coils. Guidelines for system design suited to diverse applications now and in the future, indicated that resolution may be further improved by fine-tuning the ESLA radius, ESLA separation, and ESLA operation frequency. Nevertheless, inherent trade-offs were identified in power reception and range of motion, which should be carefully accounted for during the design process.

The system may be utilized for seamless motion capture in applications as diverse as, for example, healthcare, sports, virtual reality, human-machine interfaces and gesture recognition, among others. The ESLA coils may be implemented on, for example, flexible e-textiles, and may be completely wireless and portable.

For each wearable system, at least one power source is needed to provide electrical power at least to the coil(s) that act as the transmitter(s). The power source(s) may be secured to the subject and worn as part of the wearable coil configuration or it may be separate and electrically coupled by some mechanism to the transmitter coil(s). The power source(s) may be electrically coupled by a wired connection to the transmitter coil(s) or wirelessly to the transmitter coil(s). Some type of measurement instrument, such as an ammeter or volt meter is needed to measure the electrical current or voltage, respectively, induced in the receiver coil(s). Such a measurement instrument may be secured to the subject and worn as part of the wearable coil configuration or it may be separate and electrically coupled or wirelessly connected by some means or mechanism to the receiver coil(s).

The current or voltage measurements are typically converted into digital signals and processed by one or more processors, such as one or more microcontrollers, microprocessors, application specific integrated circuits (ASICs), digital signal processors (DSPs), programmable logic arrays (PLAs), programmable gate arrays (PGAs), or other logic. The processor(s) may be secured to the subject and worn as part of the wearable coil configuration or it may be separate and electrically coupled by some means or mechanism to the measurement instrument(s). The processor(s) may be coupled by a wired connection to the measurement instrument(s) or it may be wirelessly coupled to the measurement instrument(s). In both cases, the processor(s) processes the measurement information in accordance with a motion monitoring kinematics algorithm. The motion monitoring kinematics algorithm processes the measurement information in the manner described above to determine the motion of the subject.

In the case where the processor(s) is coupled by a wired connection to the measurement instrument(s), the processor is typically part of the wearable coil configuration and is coupled to a wireless transmitter that may also be part of the wearable coil configuration. The wireless transmitter transmits the results of the algorithm to an external location, such as a remotely-located computer work station or server. The remotely-located computer work station or server would include a wireless receiver that recovers the results of the motion monitoring kinematics algorithm. In the case where the wearable coil configuration is being used to, for example, monitor the health of a patient, the remotely-located computer work station or server may be at the doctor's office of the patient. This is an example of a telemedicine application of the wearable coil configuration.

In the case where the processor(s) is coupled by a wireless connection to the measurement instrument(s), the processor(s) may be located anywhere. In this case, a wireless transmitter that may be part of the wearable coil configuration wirelessly communicates the measurement information to a wireless receiver that is electrically coupled to the processor(s). The wireless receiver then recovers the measurement information and inputs it to the processor(s) for processing in accordance with the motion monitoring kinematics algorithm. In this case, the processor(s) may be part of a remotely-located computer workstation or processing center. Some type of memory will typically be in communication with, or integrated with, the processor for storing computer code corresponding to the motion monitoring kinematics algorithm. A variety of memory devices are suitable for this purpose, including, for example, solid state memory devices such as Random Access Memory (RAM), Read Only Memory (ROM), flash memory, for example, optical memory devices and magnetic memory devices. Any such suitable memory devices are non-transitory computer-readable mediums.

It should be noted that the measurement instrument(s), the power source(s) and/or the processor(s), when part of the wearable coil configuration, may be packaged together in an electrical subsystem of the wearable system. Packaging these components together facilitates integration and/or miniaturization, which can lead to smaller and/or lighter-weight wearable systems.

XIII. System Architecture

Figure 23:
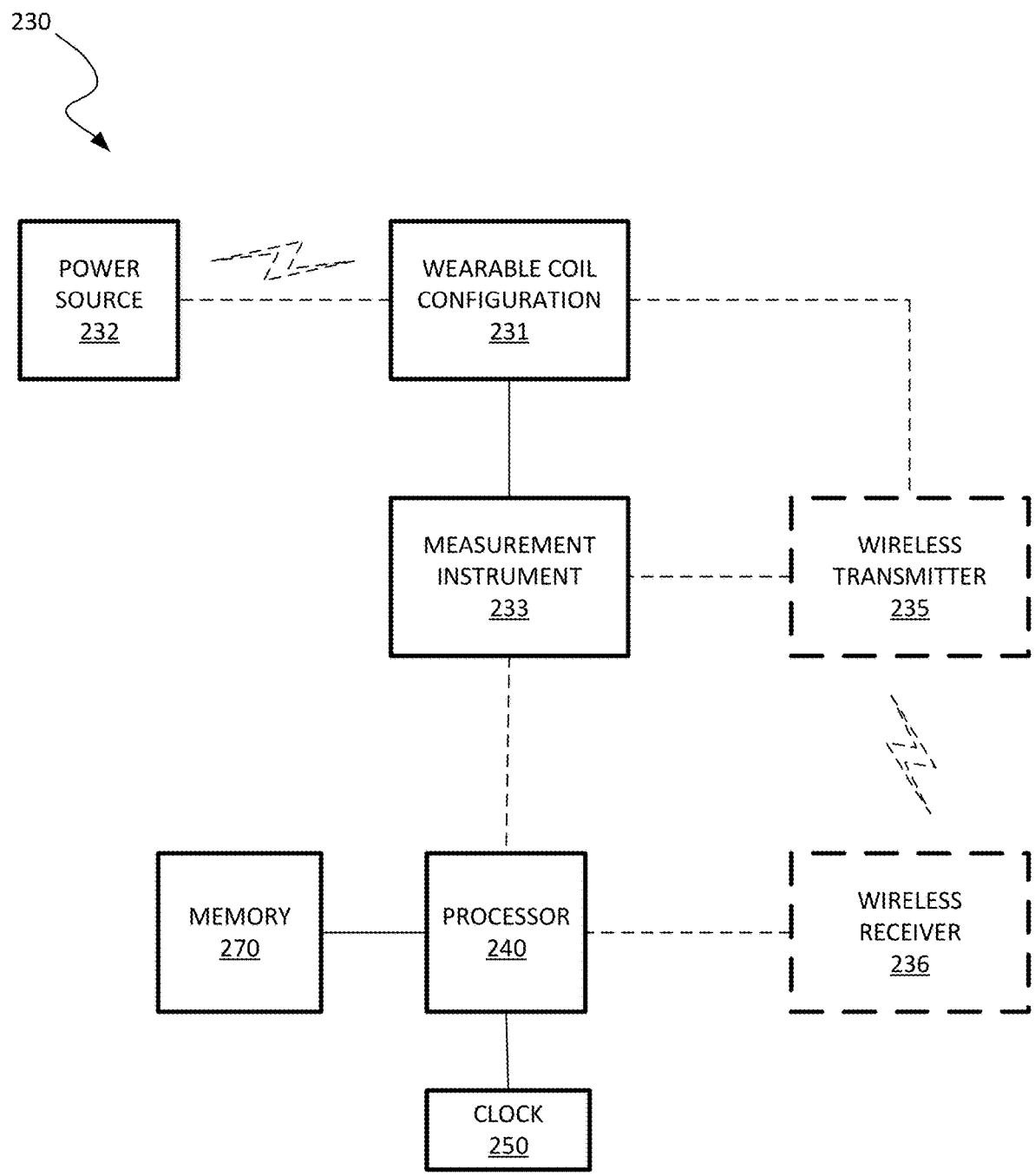
FIG. 23 is a block diagram of the system for performing monitoring body kinematics in accordance with a representative embodiment.

FIG. 23 is a block diagram of the system 230 for performing monitoring body kinematics in accordance with a representative embodiment. The dashed blocks and dashed lines in FIG. 23 represent optional components and connections, respectively, of the system 230. Solid lines represent wired connections or connections made through inductive coupling or through other types of wireless connections. Solid blocks represent components of the system 230 that are non-optional. The system 230 comprises the wearable system described above, which includes at least the wearable coil configuration 231 in accordance with any of the embodiments described above with reference FIGS. 1-22B. The wearable system typically also includes a measurement instrument 233, which may be any device that is suitable for measuring an electrical current or voltage of the Rx coil(s), such as such as an ammeter or volt meter, for example. As described above, depending on the implementation scenario, the wearable system typically also includes the power source 232 for supplying power to the wearable coil configuration 231. However, in some cases, the wearable coil configuration 231 may receive power wirelessly from an external power source, in which case the power source 232 would not be part of the wearable system, but would be part of the overall system 230.

The system 230 includes a processor 240 and a memory device 270. The processor 240 and the memory device 270 may be part of the wearable system or they may be external to the wearable system. If the processor 240 and/or memory device 270 are external to the wearable system, the system 230 will typically include the wireless transmitter 235 for communicating measurement information obtained by the measurement instrument 233 to the external components and a wireless receiver 236 for receiving information communicated to the system 230 by the external components The processor 240 is configured to perform a motion monitoring kinematics algorithm that processes the measurement information obtained by the measurement instrument 233 to obtain the motion information described above with reference to FIGS. 1-22B. If all or a portion of the algorithm is implemented in software and/or firmware, the corresponding computer code may be stored in the memory device 270, which may be any suitable non-transitory computer-readable medium, such as various types of solid state memory, magnetic memory and/or optical memory.

In a dynamic environment, the same flexion/rotation (or any other angle) measured through this system can be plotted against time. The system 230 typically includes a clock 250 that may be part of the processor 240 or external to it. The clock 250 may be used by the processor to associate sensed flexion and/or rotation events with time. The processor 240 may perform a logging algorithm that creates a log in the memory device 270 of the time at which flexion and/or rotation events occur. The processor 240 may be configured to perform a plotting algorithm that plots flexion/rotation (or any other angle) measured by the system 230 against time. Depending on the type of motion that occurs, the angles will change differently with respect to time, thereby generating different types of plots. This can aid in following:

Activity classification: For different types of motion, different types of plots of angle vs. time can be generated, which will help in activity classification, e.g., walking, running, climbing, etc. using post-processing by processor 240.

Parameter retrieval: Using the plots corresponding to each activity, different parameters such as velocity, acceleration, etc., can be determined by the processor 240 by evaluating the changes in the plot over time. For instance, for a periodic motion such as walking, a periodic plot is expected. Now, if the person changes the pace of walking, it would reflect in the change in frequency or time period of the corresponding plot. This change in frequency can thereby be used to determine acceleration. Similarly, the frequency or time period itself can be used to determine the velocity itself. Needless to mention, different points in plots would signify position or state of motion.

Any abrupt changes in these parameters can be a sign of any accident, such as fall, etc.

Once these are determined, they can be used for different applications as required or desired.

The wearable system may be implemented in a number of ways. For example, the wearable system can comprise electrically-conductive E-threads and embeddable metal coils. For coil fabrication, any metal, such as copper, can be used (e.g., embedded in wearables, clothing, or accessories like a bracelet). E-threads are electrically-conductive threads that can be used to form an antenna, coil, or other metal-based structure. E-threads can be directly woven into garments. E-threads may be used, embroidered, sewn, or knitted within the fabric. For example, a compression garment or garments of daily wear may have E-threads woven therein at preselected locations to form the transmitter and receiver coils at particular locations relative to one or more joints that are to be motion monitored.

Monitoring of most human motions can be achieved by a wearable system comprising a combination of longitudinal and transverse coil configurations described above. Such combinations have a huge potential for monitoring even fine and complex movements of the human body. These include, but are not limited to, flexion, extension, pronation, supination, abduction, adduction, fine movements of fingers and feet, head, hip and torso movements. Also, a larger number of coils can be included to increase the accuracy of the system.

It should be noted that while the inventive principles and concepts have been described with reference to monitoring human movements, they are not restricted to humans, but are equally applicable to monitoring motion of animals as well. Furthermore, the inventive principles and concepts can be extended to any other kind of motion monitoring (e.g., structural health monitoring).

It should be emphasized that the above-described embodiments of the present invention are merely possible examples of implementations, merely set forth for a clear understanding of the principles of the invention. For example, while the experiment was described with reference to particular coil configurations, other types of coil configurations may be incorporated into the wearable system. Many variations and modifications may be made to the above-described embodiments of the invention without departing from the scope of the invention. All such modifications and variations are intended to be included herein within the scope of this disclosure and the present invention.

What is claimed is:

1. A system for monitoring body kinematics, comprising:
   a wearable coil configuration comprising at least first and second electrically-conductive coils adapted to be secured to a subject at first and second locations in a predetermined spatial relationship and orientation relative to one another, the first electrically-conductive coil acting as a first transmitter of the system and generating a first magnetic flux when an electrical current is passed through the first electrically-conductive coil, the second electrically-conductive coil acting as a first receiver of the system inductively coupled to the first electrically-conductive coil, the first magnetic flux inducing a first electrical current or voltage in the second electrically-conductive coil;
   a third electrically-conductive coil adapted to be secured to the subject at a third location in a predetermined spatial relationship and orientation relative to the first and second electrically-conductive coils, the third electrically-conductive coil acting as a second receiver inductively coupled with the first electrically-conductive coil, the first magnetic flux inducing a second electrical current or voltage in the third electrically-conductive coil;
   at least a first measurement instrument configured to:
      measure the first electrical current or voltage and to output a first measurement signal; and
      measure the second electrical current or voltage and to output a second measurement signal; and
   a processor configured to execute a motion monitoring algorithm, wherein during execution of the motion monitoring algorithm, the processor processes at least the first and second measurement signals to determine at least a first motion made by the subject based upon flexion and rotation angles of the subject which are determined based upon transmission coefficients $S_{21}$ and $S_{31}$ associated with the second and third electrically-conductive coils, the transmission coefficients determined based at least in part upon the measured first and second electrical currents or voltages.

2. The system of claim 1, wherein the first and second electrically-conductive coils are adapted to be placed opposite one another relative to a joint of the subject such that use of the joint to move a portion of the subject's body that is coupled to the joint causes the position of the second electrically-conductive coil relative to the first electrically-conductive coil to change, and wherein the change in relative position produces a change in the first electrical current or voltage induced in the second electrically-conductive coil by the first magnetic flux.

3. The system of claim 2, wherein the first and second electrically-conductive coils are adapted to be placed approximately equidistant from the joint.

4. The system of claim 1, and wherein said second and third electrically-conductive coils are substantially parallel.

5. The system of claim 1, wherein the flexion and rotation angles of the subject are determined based upon magnitudes of the transmission coefficients $S_{21}$ and $S_{31}$.

6. The system of claim 1, wherein the third electrically-conductive coil acts as the second receiver of the system, the system further comprising:
   a fourth electrically-conductive coil adapted to be secured to the subject at a fourth location in a predetermined spatial relationship and orientation relative to the first, second and third electrically-conductive coils, the fourth electrically-conductive coil acting as a second transmitter, the fourth electrically-conductive coil generating a second magnetic flux when electrical current passes through the fourth electrically-conductive coil, wherein the first and second magnetic fluxes induce third and fourth electrical currents or voltages, respectively, in the second and third electrically-conductive coils, respectively.

7. The system of claim 6, wherein said at least a first measurement instrument is configured to measure the third and fourth electrical currents or voltages induced in the second and third electrically-conductive coils, respectively, and to output third and fourth measurement signals, and wherein during execution of the motion monitoring algorithm, the processor processes at least the third and fourth measurement signals to determine said at least a first motion made by the subject.

8. The system of claim 1, wherein the first and second electrically-conductive coils are configured to resonate at an operating frequency of the wearable coil configuration.

9. The system of claim 8, wherein the first and second electrically-conductive coils have first and second capacitances, respectively, that are preselected to ensure that the first and second electrically-conductive coils resonate at the operating frequency.

10. The system of claim 1, wherein the first and second electrically-conductive coils are non-resonant at an operating frequency of the wearable coil configuration.

11. The system of claim 1, wherein at least one of the first and second electrically-conductive coils is a single-turn electrically conductive coil.

12. The system of claim 1, wherein at least one of the first and second electrically-conductive coils is a multiple-turn electrically conductive coil.

13. The system of claim 1, wherein at least one of the first and second electrically-conductive coils is a transverse coil.

14. The system of claim 1, wherein at least one of the first and second electrically-conductive coils is a longitudinal coil.

15. The system of claim 1, wherein at least one of the first and second electrically-conductive coils is a longitudinal coil and at least one of the first and second electrically-conductive coils is a transverse coil.

16. The system of claim 1, wherein at least one of the first and second electrically-conductive coils is embedded in an item adapted to be worn by a subject.

17. The system of claim 16, wherein the item is an item of clothing.

18. The system of claim 17, wherein the item of clothing is customized to a size of the subject.

19. The system of claim 16, wherein the item is an accessory.

20. The system of claim 1, wherein at least one of the first and second electrically-conductive coils comprises an E-thread woven into an item adapted to be worn by a subject.

21. The system of claim 1, wherein the subject is a human being.

22. The system of claim 1, wherein the subject is a being other than a human being.

23. A system for monitoring body kinematics of a subject, the system comprising:
- a wearable coil configuration comprising at least first and second electrically-conductive coils adapted to be secured to a subject in a predetermined spatial relationship and orientation relative to one another, the first electrically-conductive coil acting as a first transmitter of the system and generating a first magnetic flux when a first electrical current is passed through the first electrically-conductive coil, the second electrically-conductive coil acting as a first receiver of the system, the first magnetic flux inducing a first electrical current or voltage in the second electrically-conductive coil;
- at least a first measurement instrument configured to measure the first electrical current or voltage and to output a first measurement signal; and
- a wireless transmitter configured to transmit a wireless signal comprising at least the first measurement signal to a remotely-located wireless receiver configured to recover the first measurement signal from the wireless signal and to provide the recovered first measurement signal to a processor that is configured to execute a motion monitoring algorithm that processes the first measurement signal to determine at least a first motion made by the subject based upon flexion and rotation angles of the subject which are determined based upon a transmission coefficient $S_{21}$ associated with the second electrically-conductive coil, the transmission coefficient determined based at least in part upon the measured first electrical current or voltage.

24. A system for monitoring health of a structure, the system comprising:
- a wearable coil configuration comprising at least first and second electrically-conductive coils adapted to be secured to a structure in a predetermined spatial relationship and orientation relative to one another, the first electrically-conductive coil acting as a first transmitter of the system and generating a first magnetic flux when a first electrical current is passed through the first electrically-conductive coil, the second electrically-conductive coil acting as a first receiver of the system, the first magnetic flux inducing a first electrical current or voltage in the second electrically-conductive coil;
- at least a first measurement instrument configured to measure the first electrical current or voltage and to output a first measurement signal; and
- a processor configured to execute a motion monitoring algorithm, wherein during execution of the motion monitoring algorithm, the processor processes at least the first measurement signal to determine a structural health of the structure based upon flexion and rotation angles of the structure which are determined based upon a transmission coefficient $S_{21}$ associated with the second electrically-conductive coil, the transmission coefficient determined based at least in part upon the measured first electrical current or voltage.

* * * * *